United States Patent
Deacon et al.

(10) Patent No.: US 10,350,059 B2
(45) Date of Patent: Jul. 16, 2019

(54) OCULAR IMPLANT INSERTION APPARATUS AND METHODS

(71) Applicant: HOYA CORPORATION, Tokyo (JP)

(72) Inventors: Jim Deacon, Goleta, CA (US); John Scholl, San Ramon, CA (US); Takashi Ichinohe, Singapore (SG); Thomas McNicholas, Laguna Niguel, CA (US); Christopher James Glaister, San Francisco, CA (US); Christopher A. Wilson, Fremont, CA (US); Phillip C. Halbert, San Francisco, CA (US)

(73) Assignee: Hoya Corporation, Tokyo (JP)

( * ) Notice: Subject to any disclaimer, the term of this patent is extended or adjusted under 35 U.S.C. 154(b) by 360 days.

(21) Appl. No.: 14/649,908

(22) PCT Filed: Dec. 4, 2013

(86) PCT No.: PCT/US2013/073201
§ 371 (c)(1),
(2) Date: Jun. 4, 2015

(87) PCT Pub. No.: WO2014/089250
PCT Pub. Date: Jun. 12, 2014

(65) Prior Publication Data
US 2015/0342726 A1 Dec. 3, 2015

Related U.S. Application Data

(60) Provisional application No. 61/733,534, filed on Dec. 5, 2012, provisional application No. 61/801,897, filed on Mar. 15, 2013.

(51) Int. Cl.
*A61F 2/16* (2006.01)
*A61F 2/14* (2006.01)

(52) U.S. Cl.
CPC ............. *A61F 2/167* (2013.01); *A61F 2/148* (2013.01); *A61F 2/1662* (2013.01); *A61F 2/1664* (2013.01); *A61F 2/1678* (2013.01)

(58) Field of Classification Search
CPC .... A61F 2/148; A61F 2/1662; A61F 2/16667; A61F 2/167; A61F 2/1672; A61F 2/1678; A61F 2/1664
See application file for complete search history.

(56) References Cited

U.S. PATENT DOCUMENTS

| | | | |
|---|---|---|---|
| 3,945,379 A * | 3/1976 | Pritz | A61M 5/30 604/70 |
| 4,834,094 A | 5/1989 | Patton et al. | |

(Continued)

FOREIGN PATENT DOCUMENTS

| | | |
|---|---|---|
| DE | 196 14 337 A1 | 8/1997 |
| EP | 0937443 B1 | 5/2004 |

OTHER PUBLICATIONS

Supplementary European Search Report dated Jul. 26, 2016 in corresponding EPO App. Serial No. 13861297.3.

(Continued)

*Primary Examiner* — Sarah A Simpson
(74) *Attorney, Agent, or Firm* — Henricks Slavin LLP

(57) ABSTRACT

An ocular implant insertion apparatus that includes a plunger driver that is not manually powered and ocular implant insertion methods. There are a variety of instances where an ocular implant is inserted into the anterior chamber, posterior chamber, cornea, vitreous space and/or other portion of an eye. Exemplary ocular implants include, but are not limited to, lenses, capsular tension rings, ocular prosthesis and lamellar transplants.

18 Claims, 19 Drawing Sheets

(56) References Cited

U.S. PATENT DOCUMENTS

| | | | |
|---|---|---|---|
| 4,836,201 A | 6/1989 | Patton et al. | |
| 8,998,983 B2* | 4/2015 | Auld | A61F 2/1678 |
| | | | 606/107 |
| 9,393,370 B2* | 7/2016 | Auld | A61M 5/2046 |
| 2008/0097460 A1 | 4/2008 | Boukhny et al. | |
| 2008/0097461 A1* | 4/2008 | Boukhny | A61F 2/1678 |
| | | | 606/107 |
| 2009/0292293 A1 | 11/2009 | Bogaert et al. | |
| 2011/0009874 A1 | 1/2011 | Wardle et al. | |
| 2011/0301538 A1 | 12/2011 | Stammen et al. | |
| 2014/0200588 A1* | 7/2014 | Anderson | A61F 2/167 |
| | | | 606/107 |

OTHER PUBLICATIONS

PCT International Preliminary Examination Report dated Feb. 25, 2014 in corresponding PCT App. Serial No. PCT/US2013/073201.

* cited by examiner

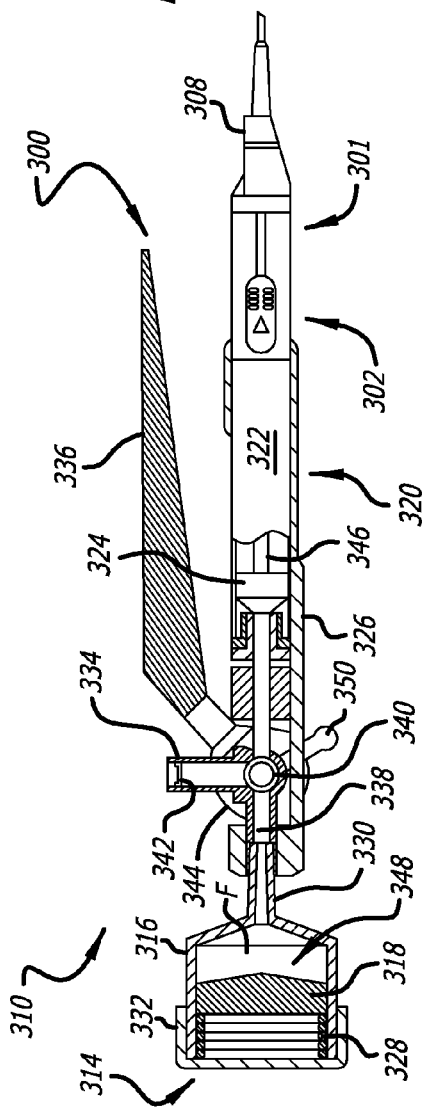
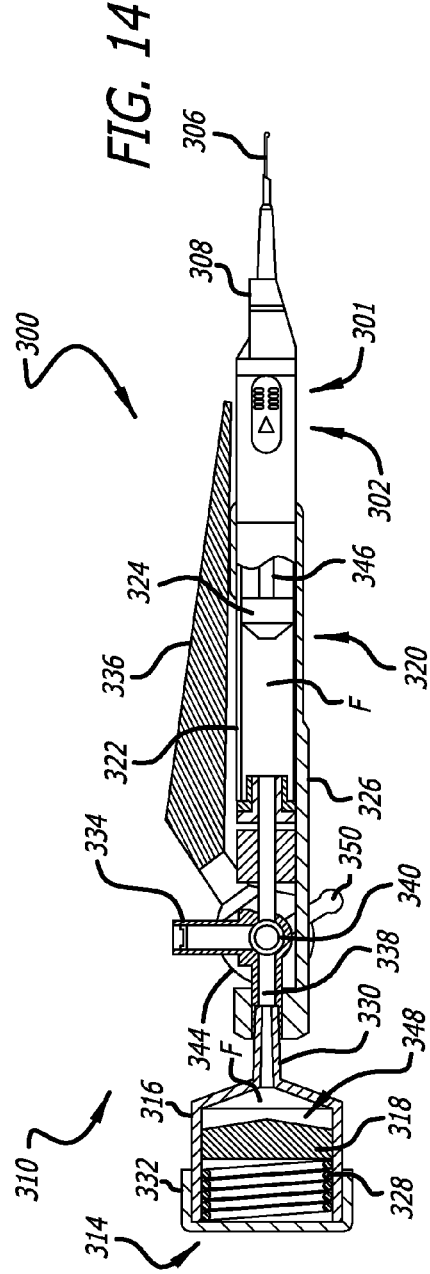

OCULAR IMPLANT INSERTION APPARATUS AND METHODS

CROSS-REFERENCE TO RELATED APPLICATION

This application is the U.S. National Stage of PCT App. Ser. No. PCT/US2013/073201, filed Dec. 4, 2013, which claims the benefit of U.S. Provisional Application No. 61/733,534, filed Dec. 5, 2012, and U.S. Provisional Application No. 61/801,897, filed Mar. 15, 2013, both of which are incorporated herein by reference.

BACKGROUND OF THE INVENTIONS

1. Field of the Inventions

The present inventions relate generally to apparatus for inserting an ocular implant into an eye.

2. Description of the Related Art

There are a variety of instances where an ocular implant is inserted into the anterior chamber, posterior chamber, cornea, vitreous space and/or other portion of an eye. Exemplary ocular implants include, but are not limited to, lenses, capsular tension rings, ocular prosthesis and lamellar transplants. An intraocular lens (IOL), for example, may be inserted into an aphakic eye that has undergone a cataract surgery or may be inserted into a phakic eye during a refractive surgery. One type of lens is a foldable lens. Foldable lenses are formed from soft material such as a silicone elastomer, soft acrylic, or hydrogel and may be inserted into the eye through a small incision. Lens insertion apparatus, which may be used to push a foldable lens into an eye through a nozzle, generally include screw-type insertion apparatus and push-type insertion apparatus. In both cases, the lens insertion apparatus may include a plunger that is used to push a folded lens through the nozzle into the eye by way of an incision that is relatively small, e.g., an incision that is smaller than the diameter of an IOL optic.

Loading an ocular implant into an inserter can be a troublesome portion of the insertion procedure. The implant may be contaminated, damaged or improperly placed into the inserter by operator, e.g., a surgeon or assistant. Accordingly, in some instances, the insertion apparatus is preloaded, i.e., the insertion apparatus is shipped from the factory with the ocular implant (e.g., an IOL) stored therein. An operator using a preloaded inserter does not place the implant into the insertion apparatus, thereby eliminating the possibility of the aforementioned operator error associated with loading. The IOL or other ocular implant may be stored in an unstressed state and then, prior to the implantation process, folded into a small state prior to being pushed through the nozzle. In some instances, the plunger alone is used to move the lens through the folding and insertion processes. In other instances, insertion apparatus have been configured to fold and move an IOL in stepwise fashion through the use of multiple IOL moving structures. Examples of such insertion apparatus are illustrated and described in U.S. Pat. Pub. Nos. 2011/0082463 and US2001/0007942 and PCT Pub. No. WO 2011/155636, which are incorporated herein by reference.

The present inventors have determined that conventional ocular implant insertion apparatus are susceptible to improvement. For example, the present inventors have determined that conventional insertion apparatus sometimes require the use of both hands when the plunger is driving the IOL or other ocular implant into the eye. In particular, some conventional insertion apparatus that facilitate precise control of plunger movement employ a rotatable handle that is configured, and connected to the plunger, such that rotation of the handle relative to the remainder of the insertion apparatus results in linear movement of the plunger. One hand is required to rotate the handle, while the other hand is required to prevent rotation of the remainder of the insertion apparatus. As a result, the surgeon does not have a free hand that could be used to control the eye or to operate an instrument that is being employed in conjunction with the insertion apparatus.

SUMMARY

An exemplary ocular implant insertion apparatus includes a housing including an ocular implant storage area and a nozzle, a plunger movable in a distal direction relative to the housing, and a non-manually driven plunger driver that is configured to drive the plunger in the distal direction.

There are a number of advantages associated with such an insertion apparatus. For example, the use of a plunger driver that is not manually driven allows the surgeon to operate the insertion apparatus with one hand while the ocular implant is being inserted into the eye. As a result, the other hand can be used to control the eye or to operate another instrument.

BRIEF DESCRIPTION OF THE DRAWINGS

Detailed description of exemplary embodiments of the inventions will be made with reference to the accompanying drawings.

FIG. 13 is a partial section view of the IOL insertion apparatus illustrated in FIG. 9.

FIG. 14 is a partial section view of the IOL insertion apparatus illustrated in FIG. 9.

DETAILED DESCRIPTION OF EXEMPLARY EMBODIMENTS

Figure 1:
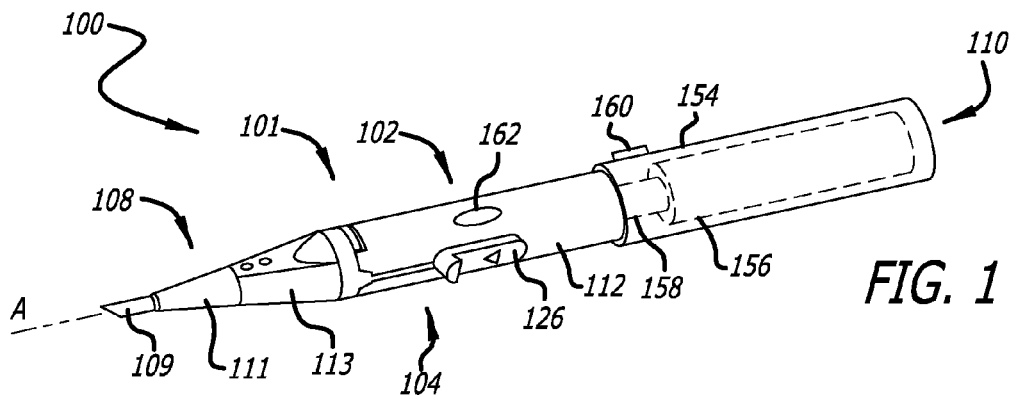
FIG. 1 is a perspective view of an IOL insertion apparatus in accordance with one embodiment of a present invention.

The following is a detailed description of the best presently known modes of carrying out the inventions. This description is not to be taken in a limiting sense, but is made merely for the purpose of illustrating the general principles of the inventions. The present inventions are also applicable to a wide variety of ocular implants which, as used herein, refers to any structure, instrumentality or device that is placed into any ocular structure or region. Ophthalmic lenses, capsular tension rings, ocular prosthesis and lamellar transplants are examples of ocular implants. Although the exemplary implementations are described below in the context of an intraocular lens (IOL), the present inventions are also applicable other types of ocular implants, including those yet to be developed. For example, the present inventions are applicable to other types of ophthalmic lenses. Such lenses include, but are not limited to, intraocular contact lenses, phakic IOLs, and other lenses that may be inserted into the eye. Also, movement of the movable components of an insertion apparatus and the IOL towards the eye is referred to herein as movement in the forward (or "distal") direction and movement away from the eye is referred to herein as movement in the rearward (or "proximal") direction.

As illustrated in FIGS. 1-7, the exemplary IOL insertion apparatus 100 is a preloaded insertion apparatus and, to that end, an IOL 10 is placed within the insertion apparatus during the assembly process and the insertion apparatus is shipped and stored with the IOL located therein. In the illustrated implementation, the IOL 10 (FIG. 3) includes an optic 12 and a pair of supports 14 and 16 such as, for example, the illustrated pair of haptics. The exemplary IOL insertion apparatus 100 includes an inserter 101, with a main body 102, a slider 104, a plunger 106 and an insertion tube 108 that is mounted on the forward end of the main body after the IOL is in place, and a plunger driver 110 that is operably connected to the inserter, e.g., to the main body and the plunger. The main body 102 and insertion tube 108 together define the housing of the inserter 101. The slider 104 and plunger 106 are movable relative to the housing and relative to each other. Although the present inventions are not so limited, the exemplary IOL insertion apparatus 100 is substantially similar to the IOL insertion apparatus illustrated in PCT Pub. No. WO 2011/155636, which is incorporated herein by reference in its entirety. Here, however, the plunger 106 is not manually driven as it is in PCT Pub. No. WO 2011/155636 and, instead, is driven by the plunger driver 110 in the manner described below. In other words, the force required to drive the plunger 106 in the distal direction is not supplied by the surgeon and is instead supplied by the plunger driver 110.

Figure 2:
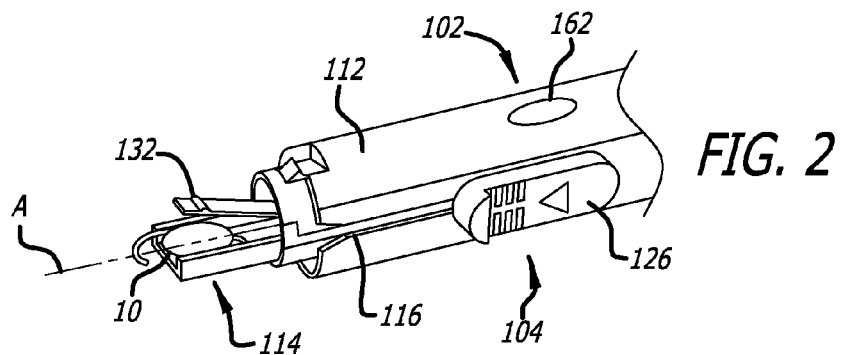
FIG. 2 is a perspective view of the main body of the exemplary IOL insertion apparatus illustrated in FIG. 1.
Figure 3:
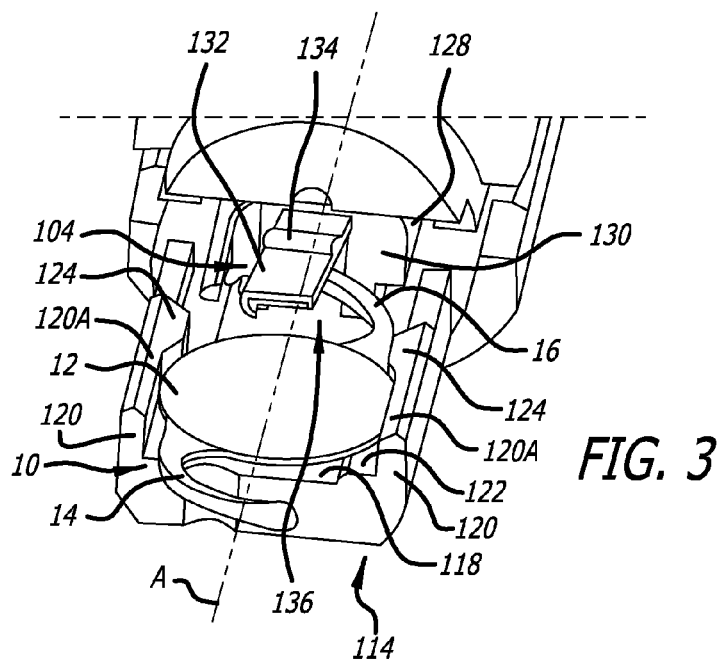
FIG. 3 is another perspective view of the main body of the exemplary IOL insertion apparatus illustrated in FIG. 1.

Referring to FIGS. 1-3, the exemplary main body 102 includes a tubular member 112, a lens placement section 114, and a slider guide section 116. The lens placement section 114 protrudes distally from the front end of the tubular member 112. The insertion tube 108 in the illustrated embodiment has a nozzle 109, a transition section 111, and a protector 113 that is positioned over the lens placement section 114, with interior regions that are in communication with one another so that an IOL can pass therethrough. The insertion tube 108 is connected to the main body 102 by a connector arrangement. The inner diameter of the transition section 111 tapers downwardly from the end adjacent to the protector 113 to the end adjacent the nozzle 109. The slider guide section 116, which is configured to allow the slider 104 to move forwardly and rearwardly, may be a pair of slits formed in the tubular member 112 that are parallel to the lens advancement axis A. The slider guide section 116 also extends rearwardly from the distal end of the tubular member 112 to the central portion of the tubular member.

The exemplary lens placement section 114 (FIG. 3) includes a bottom surface 118, a pair of side walls 120 respectively located on opposite sides of the bottom surface and extending upwardly from the bottom surface, and a pair of rails 122. The bottom surface 118 and the side walls 120 are parallel to the lens advancement axis A and the lens advancement axis A is located between the side walls. The side walls 120 each include, near the upper end, an inclined surface 120A. The rear portions of the side walls 120 include inward protrusions 124 that prevent the IOL 10 from moving in the rearward direction. The lens supporting surfaces of the rails 122 are oriented in a direction that is transverse to the lens advancement axis A and slope away from the axis A in the rearward to forward direction. As such, the stored IOL 10 is tilted relative to the lens advancement axis A, with the forward end of the IOL optic 12 closer to the bottom surface 118 than the rearward end. The lens supporting surfaces of the rails 122 are also located a sufficient distance above the bottom surface 118 to prevent the IOL optic 12 from coming into contact with the bottom surface.

It should be noted that references herein to "top," "bottom," "upward," "downward" and the like are merely references to the illustrated orientation and/or the relationship of the components relative to one another in the illustrated orientation. For example, the side of the IOL 10 facing the bottom surface 118 is referred to "the downward side" and movement toward the bottom surface is referred to as movement in the "downward direction," while the opposite side of the IOL 10 is referred to as the "the upward side" and movement away from the bottom surface 118 is referred to as movement in the "the upward direction."

Figure 6:
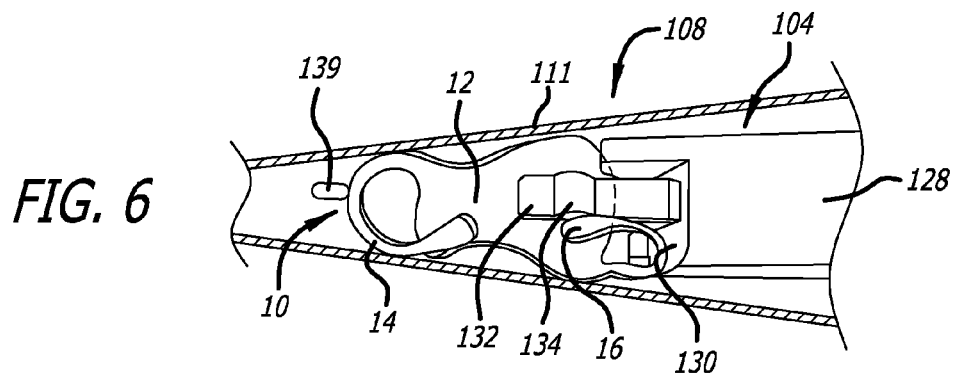
FIG. 6 is a partial section view showing an aspect of the operation of the exemplary IOL insertion apparatus illustrated in FIG. 1.

Turning to the exemplary slider 104 illustrated in FIGS. 2, 3 and 6, the slider includes a pair of grips 126, an elongate member 128 with a lens contact surface 130 that is carried within the main body 102 and is slidable relative thereto. The grips 126 are connected to elongate member 128. The lens contact surface 130, which is larger than the plunger distal end 144 (discussed below), is used to scoop up the proximal IOL support 16 during the initial folding of the IOL 10. A lens holder 132 is pivotably mounted on the distal end of elongate member 128 and includes a protrusion 134. The lens holder 132 controls the initial folding of the IOL 10 during the first step of the lens insertion process. More specifically, as the slider 104 moves distally, the protrusion 134 rides along the tapered inner surface of the transition section 111, which causes the lens holder 132 to pivot downwardly into contact with the IOL optic 12 to fold the IOL 10. A protrusion 139 (FIG. 6) may be used to deflect the leading haptic 14. The slider elongate member 128 also includes a slot 136 through which the plunger rod 138 (discussed below) passes during the second step of the insertion process.

Figure 4:
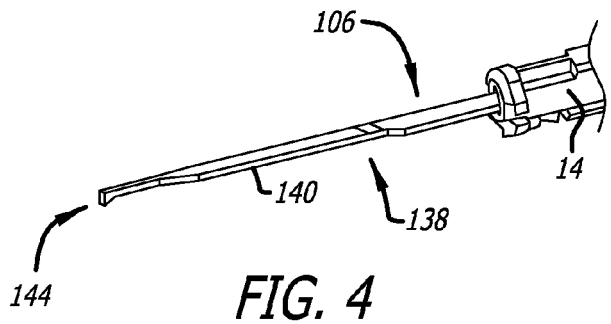
FIG. 4 is a perspective view of the plunger of the exemplary IOL insertion apparatus illustrated in FIG. 1.
Figure 5:
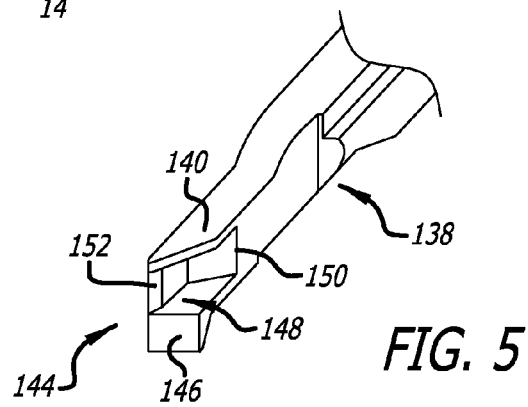
FIG. 5 is another perspective view of the plunger of the exemplary IOL insertion apparatus illustrated in FIG. 1.

As illustrated in FIGS. 4 and 5, the exemplary plunger 106 includes a rod 138 with a distal rod portion 140, a proximal rod portion 142, and a rod distal end 144. The distal rod portion 140, which is sized such that it can be inserted through the nozzle 109, may be connected to, or may be integral with, the proximal rod portion 142. As illustrated for example in FIG. 6, the rod distal end 144 may have a lens contact portion 146 and a recess 148 in which the free end of the proximal IOL support 16 is located during the second step of the two-step process. The exemplary lens contact portion 146 is a planar surface that is perpendicular to the lens advancement axis A, and is provided on a lower portion of the rod distal end 144. The exemplary recess 148, which has an opening 150 on one lateral side and a wall 152 on the other lateral side, is located above the lens contact portion 146. The recess 148 may be formed by cutting (or otherwise removing) material from the rod distal portion 140, starting at the distal end 144, or by molding the rod in the illustrated configuration. The wall 152 engages the outer edge of the IOL optic 12 and prevents optic of the folded IOL 10 from entering the recess 148. The wall 152 also keeps the IOL support 16 within the recess 148. The distal end of the wall 152 may be in the same plane as the lens contact portion 146 (as shown) or may be located distally beyond the lens contact portion 146. The proximal rod portion 142 is operably connected to the plunger driver 110 in the manner described below.

The plunger driver 110 may be secured to and/or supplied with the inserter 101 (including the preloaded IOL 10) in a variety of ways. Briefly, and for example, the plunger driver 110 may be a permanent portion of the insertion apparatus 100. As used herein, a "permanent portion" of an apparatus is a portion that, subsequent to assembly, is not removed during normal usage and cannot be removed without destruction of the associated connector or some other portion of the apparatus. Such an insertion apparatus may, in some instances, be a single use device that is shipped from the manufacturer in a sterile state. Alternatively, the plunger driver 110 may be supplied separately from the inserter 101 and secured to the inserter to form the insertion apparatus 100 at the time of use. Such a plunger driver may be a single-use device, or a reusable device, that is attached to the inserter 101 within the sterile field. A single-use plunger driver may be supplied separately in a sterile state, while a reusable plunger driver will be sterilizable. In some instances, a power cable may be required. The cable (not shown) may be a permanent portion of the associated plunger driver that is shipped in a sterile state (e.g., with the plunger driver or the entire insertion apparatus), or may be a separate device that is connected to the plunger driver within the sterile field. In some instances, a fluid tube may be required to convey liquid or gas from a separate source to the plunger driver. The fluid tube (not shown) may be a permanent portion of the associated plunger driver that is shipped in a sterile state (e.g., with the plunger driver or the entire insertion apparatus), or may be a separate device that is connected to the plunger driver within the sterile field.

Figure 7:
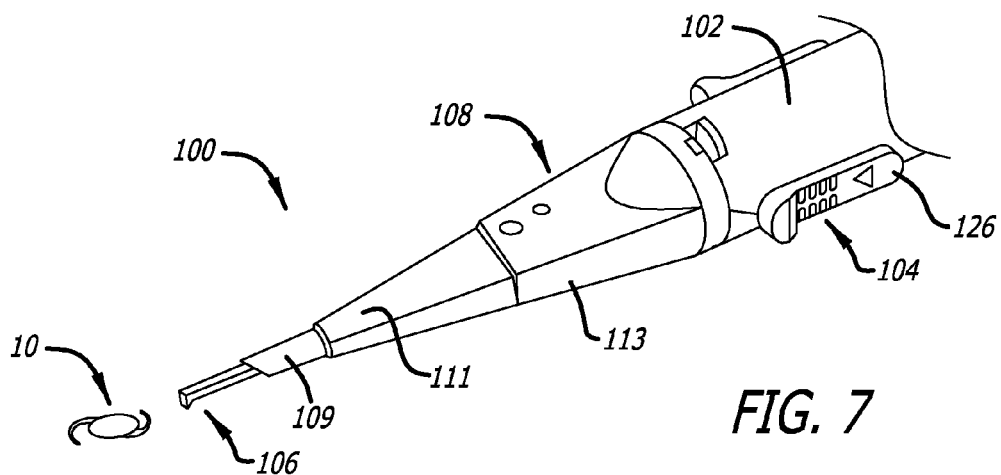
FIG. 7 is a perspective view showing another aspect of the operation of the exemplary IOL insertion apparatus illustrated in FIG. 1.

Referring to FIG. 1, the exemplary plunger driver 110 includes a housing 154, a drive mechanism 156 and a linkage 158 that operably connects the drive mechanism to the plunger 106 such that operation of the drive mechanism results in distal linear movement of the plunger from an initial storage position to the fully deployed position (FIG. 7). In some instances, the linkage may be omitted and the drive mechanism may be connected directly to the plunger 106.

As alluded to above, a wide variety of drive mechanisms may be employed. Such drive mechanisms include, but are not limited to, torsion springs, linear springs (tension or compression), electric motors, solenoids and other electrically powered devices, hydraulic devices where the fluid is pumped during the procedure, pressurized gas and other pneumatic devices (e.g., a cartridge filled compressed $CO_2$, or some other compressed gas, that is connected to a piston or turbine), devices that create gas pressure through exothermic chemical reactions, magnetic devices (either electromagnetic or a permanent magnet), rotating flexible cables (one end associated with the plunger driver and the other end connected to a motor or other source of rotational force) and combinations of such mechanisms (or "hybrid mechanisms"). The configuration of the linkage 158 will depend upon the configuration of the drive mechanism 156. For example, a screw-thread linkage may be combined with a rotating drive mechanism. Various other exemplary plunger drivers and drive mechanisms are described below with reference to FIGS. 9-32.

The device that is used to actuate the plunger driver 110 will also depend upon the type of drive mechanism that is employed. In the illustrated implementation, the drive mechanism 156 is a torsion spring that may be supplied in a state where it is storing mechanical energy. In other implementations, the torsion spring may be armed at or near the time of use by rotating one portion of the spring relative to another. This may be accomplished by, for example, rotating one portion of the insertion apparatus housing relative to another (e.g., the driver housing 154 is a two-part structure where one part is rotatable relative to the other), rotating a small removable or permanent crank handle that is connected to spring, rotating an oversized grip handle that is connected to the spring and used only for rotating the spring, or using a reusable motor driven crank that can be disconnected from the plunger driver after the spring is armed. Whether the spring is supplied in an armed state or is armed at the time of use, a latch (not shown) may be used to maintain the torsion spring in this state. An actuation button 160 releases the latch in the illustrated embodiment.

Similarly, the manner in which movement of the plunger 106 is controlled as it is being driven by the drive mechanism will depend upon the type of drive mechanism that is employed. A friction brake (not shown) may be used by the surgeon to selectively control (e.g., stop, start, slow) the movement of the plunger 106. In the illustrated embodiment, the brake is biased to the engaged state that prevents plunger movement and is released when a button 162 is pressed. In other implementations, the brake is biased to a disengaged stated and the button 162 may be used to apply the brake. In still other implementations, the button 162 may be used to stop movement of the plunger by, for example, disconnecting an electrical drive mechanism from a power source, shunting fluid in context of a hydraulic drive mechanism, or venting gas in the context of a pneumatic drive mechanism. In some implementations, a single button (e.g., the button 162) may be used for both actuation and control/braking.

Other aspects of plunger movement that can be controlled by way of the button 162, footswitch or other control instrumentality include the speed and direction of the plunger. In particular, the control instrumentality (which may take the form of multiple separately actuated instrumentalities) may be used to increase or decrease the speed of the plunger and/or to change the plunger direction of movement from forward to reverse and from reverse to forward. The manner in which such control may be accomplished will depend upon the drive mechanism employed. For example, motors and other electrically powered drive mechanisms may be controlled with conventional power control techniques.

The insertion apparatus 100 may also be configured such that, upon actuation of the drive mechanism 156, the plunger will move to a predetermined location proximal of the nozzle 109 prior to assumption of control by the surgeon. For example, the insertion apparatus 100 may be configured such that plunger 106 moves distally until the plunger distal end 144 reaches the proximal end of the folded IOL 40 (note the IOL location in FIG. 6). The movement of the plunger 106 may then be automatically stopped, i.e., stopped without additional action by the surgeon, and additional movement will require an action by the surgeon (e.g., pressing button 162).

Operation of the exemplary insertion apparatus 100, where the IOL is pushed out of the apparatus and into the eye, is referred to herein as a "push-out" or "insertion" process. The slider 104, which has a pair of finger grips 126, performs the first step in the insertion process, i.e., folding a previously unstressed IOL into a particular configuration, and may therefore be referred to as one example of a first lens push-out mechanism. The exemplary slider 104 pushes the IOL 10 distally as it folds the IOL. In other implementations, the first "push-out" mechanism may perform the first step of the "push-out" process by simply folding an IOL without moving it distally. The exemplary plunger 106 performs the second step in the insertion process, i.e., pushing the folded IOL through a tapered lumen and then into the eye, and may therefore be referred to as one example of a second lens push-out mechanism. The IOL moves along a lens advancement axis A during the insertion process. In the illustrated implementation, distal movement of the plunger 106 commences upon actuation of the drive mechanism 156 through operation of the button 160, and is subsequently controlled through operation of the button 162. Thus, the present inventions allow the surgeon to perform the second step with one hand. In particular, the present inventions allow the surgeon to both hold the insertion apparatus 100, and control movement of the plunger 106, with the same hand.

It should be noted here that, in some instances, it may be desirable to heat the IOL prior to and/or during the push-out process to increase the flexibility of the IOL. Heat may be supplied in a variety of ways. For example, those embodiments of where the plunger driver 106 creates heat (e.g., those that employ an exothermic chemical reaction), the heat may be transferred to the region of the insertion apparatus (e.g., a portion of the insertion tube) in which the IOL is located. A heat pipe is one example of device that could transfer heat from the drive mechanism to the region in which the IOL is located. Alternatively, a separate heating element may be employed. In those instances where the plunger driver 106 is electrically powered, some of the electricity stored in or delivered to the insertion apparatus may be used to power the heating element (e.g., a heating coil or other resistance based heater). Such a heating element could be embedded in and extend around, for example, the protector 113 of the insertion tube 108.

It should also be noted that heating elements may be employed in ocular implant insertion apparatus that do not include a powered plunger driver. For example, a heating element may be provided on manually powered insertion apparatus such as those described in U.S. Pat. Pub. Nos. 2011/0082463 and US2001/0007942 and PCT Pub. No. WO 2011/155636.

Figure 8:
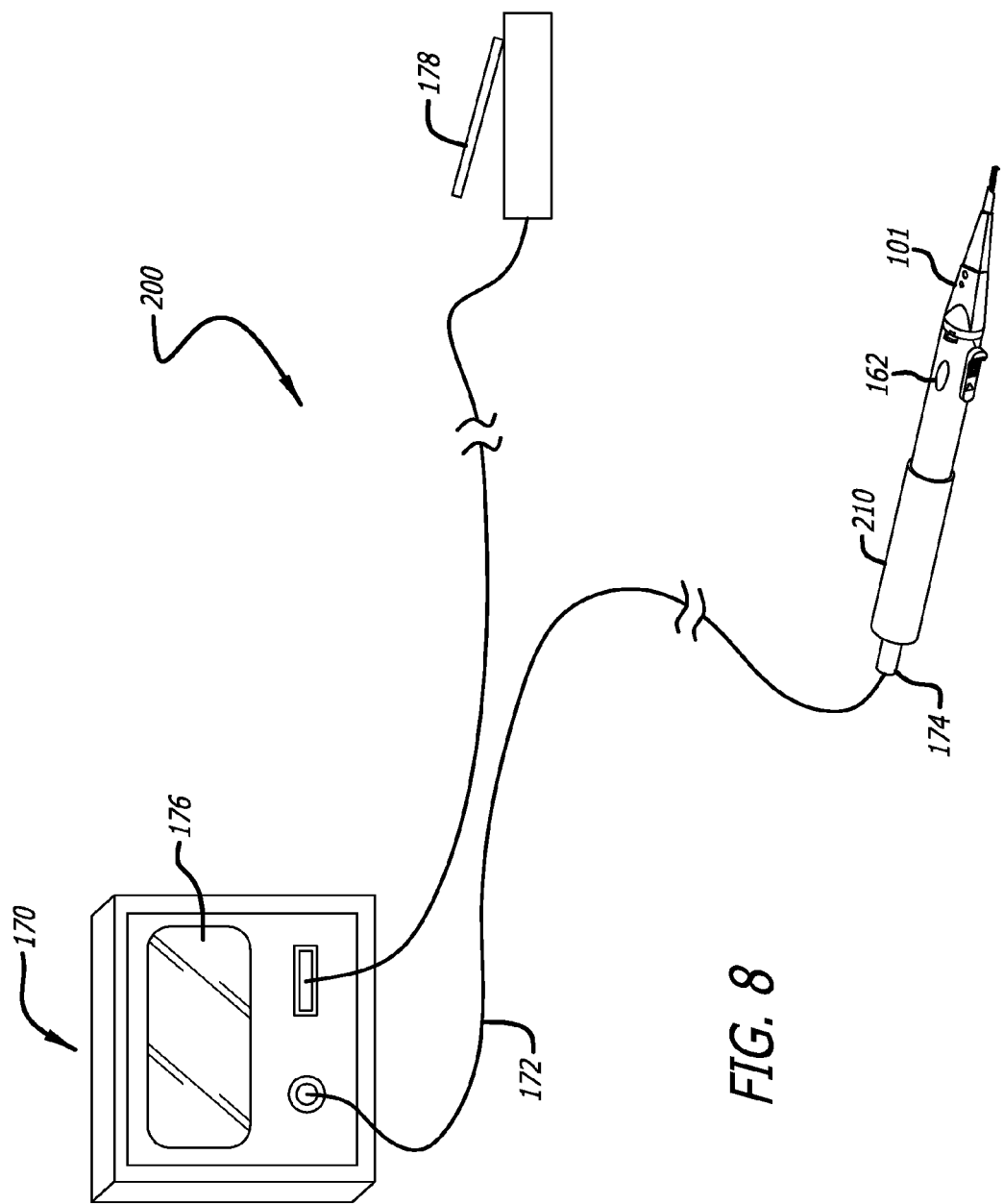
FIG. 8 is a perspective view of an IOL insertion system in accordance with one embodiment of a present invention.

Turning to FIG. 8, the exemplary IOL insertion system illustrated therein includes an exemplary IOL insertion apparatus 200, with an inserter 101 (described above) and a plunger driver 210, and power supply and control unit 170. The plunger driver 210 and control unit 170 drive the plunger, and control the movement thereof, through the use of apparatus including, but not limited to, electric motors, solenoids and other electrically powered devices, hydraulic devices where the fluid is pumped during the procedure, pressurized gas and other pneumatic devices, devices that create gas pressure through exothermic chemical reactions, magnetic devices, and rotating flexible cables (one end associated with the plunger driver and the other end connected to a motor or other source of rotational force). Operation of the control unit 170, which is connected to the insertion apparatus 200 by a cable 172 and a connector 174, is responsive to the button 162, a touchscreen 176, and/or a footswitch 208 to facilitate control of the plunger in the manner described above. For example, the control unit 170 may include electrical power supply and power to an electric motor that drives the plunger may be controlled by a processor in the control unit in response to operation of the button 162, touchscreen 176, and/or footswitch 208. Wireless control may also be employed. The control unit 170 would be a reusable device, while the insertion apparatus could be either a single use or a reusable device.

Figure 9:
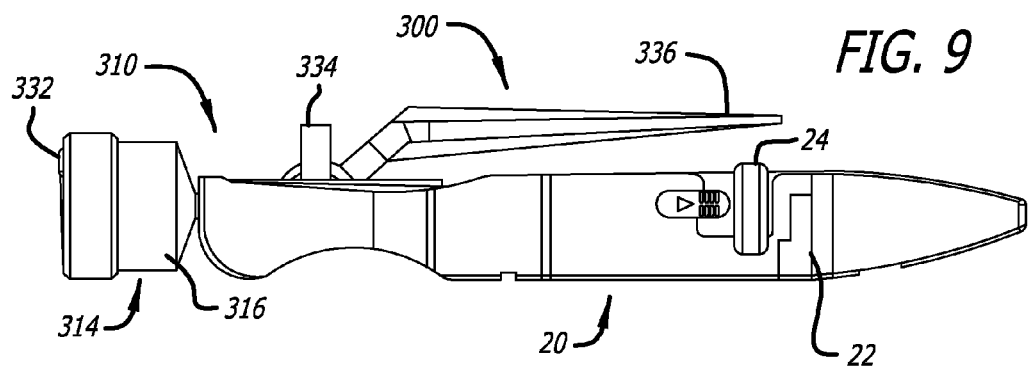
FIG. 9 is a side view of an IOL insertion apparatus in accordance with one embodiment of a present invention.
Figure 10:
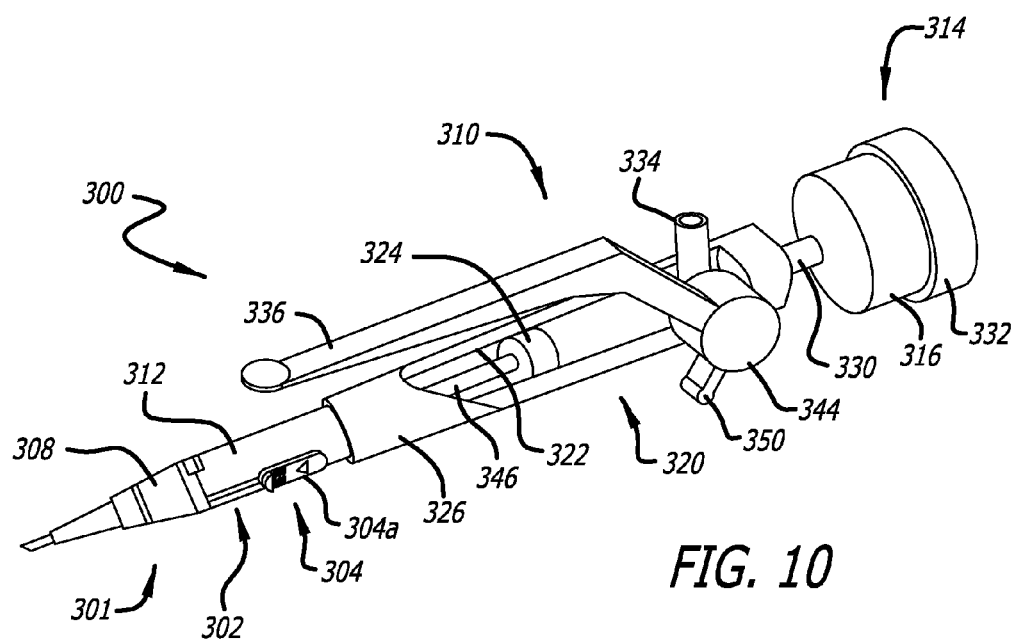
FIG. 10 is a cutaway, perspective view of the IOL insertion apparatus illustrated in FIG. 9.

Another exemplary IOL insertion apparatus is generally represented by reference numeral 300 in FIGS. 9 and 10. The exemplary insertion apparatus 300, which is shown in FIG. 9 within a case 20, includes an inserter 301 and a plunger driver 310. The inserter 301 (FIG. 10) is substantially similar to the inserter 101 and similar elements are represented by similar reference numerals. To that end, the inserter 301 includes components, such as a main body 302 with a tubular member 312, a slider 304, a plunger 306 (FIG. 14) and an insertion tube 308, that operate in the manner described above with reference to inserter 101. For example, the slider 304 includes grips 304a and an elongate member (not shown) that moves with the grips to fold an IOL as is discussed above with reference to FIGS. 2, 3 and 6. The case 20, which includes an enclosure 22 and a cover 24, protects the inserter 301 and prevents erroneous operation thereof in the manner described in PCT Pub. No. WO 2011/155636.

Turning to the plunger driver, the exemplary plunger driver 310 illustrated in FIGS. 9 and 10 employs a drive mechanism that is a hybrid device that includes a hydraulic drive mechanism which is powered by a spring. The plunger driver 310 includes a master cylinder 314, with a cylinder body 316 and a piston 318 (FIG. 11) within the cylinder body, and a slave cylinder 320, with a cylinder body 322 and a piston 324 located within the cylinder body. An external driver housing 326 to which, or in which, the plunger driver components are mounted is also provided. The inserter 301 is also mounted to the driver housing 326 by way of the tubular member 312. The piston 318 is driven by a spring 328 (FIG. 11) that is also located within the cylinder body 316. A tube 330 connects the master cylinder 314 to the slave cylinder 320. A cap 332 is used to close the end of the cylinder body 316, after the piston 318 and spring 328 have been inserted, during the assembly process. The plunger driver 310 also includes a fluid port 334 that receives the hydraulic fluid (e.g., sterile saline) during the priming process, as is discussed below, and an actuation handle 336.

Figure 11:
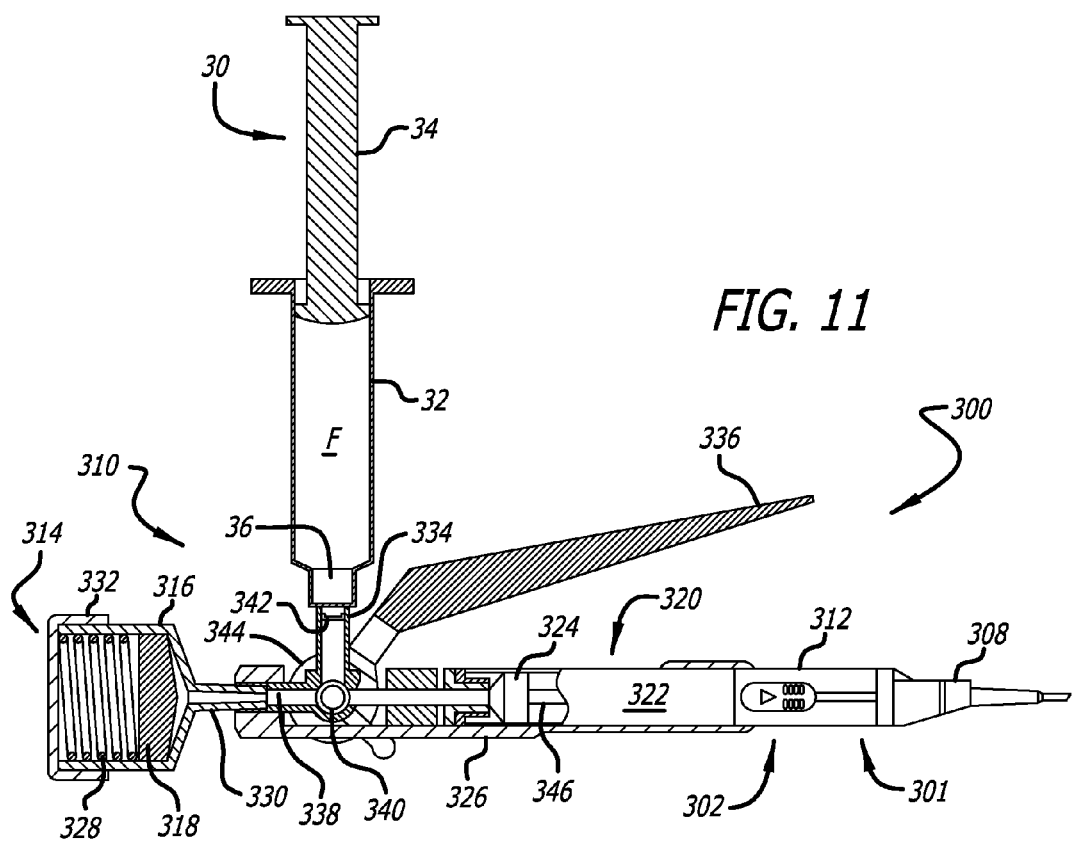
FIG. 11 is a partial section view of the IOL insertion apparatus illustrated in FIG. 9.

Referring to FIG. 11, the plunger driver also includes a tube 338 with an inlet associated with the master cylinder 314 and an outlet associated with the slave cylinder 320. A multi-position valve 340 controls the flow of fluid through the tube 338, and a one-way valve 342 controls the flow of fluid through the port 334. The valve 340 includes a rotatable control shaft (not shown) that is connected to the handle 336 by a hub 344. As such, the user can control the valve 340 by moving the handle 336 as is discussed below. It should also be noted here that the diameter of the master cylinder body 316 is substantially greater than the slave cylinder body 322. The increased diameter facilitates the use of a master cylinder 314 that is shorter than the slave cylinder 320, thereby reducing the overall length of the apparatus. A rod 346 connects the piston 324 to the inserter plunger 306.

Figure 12:
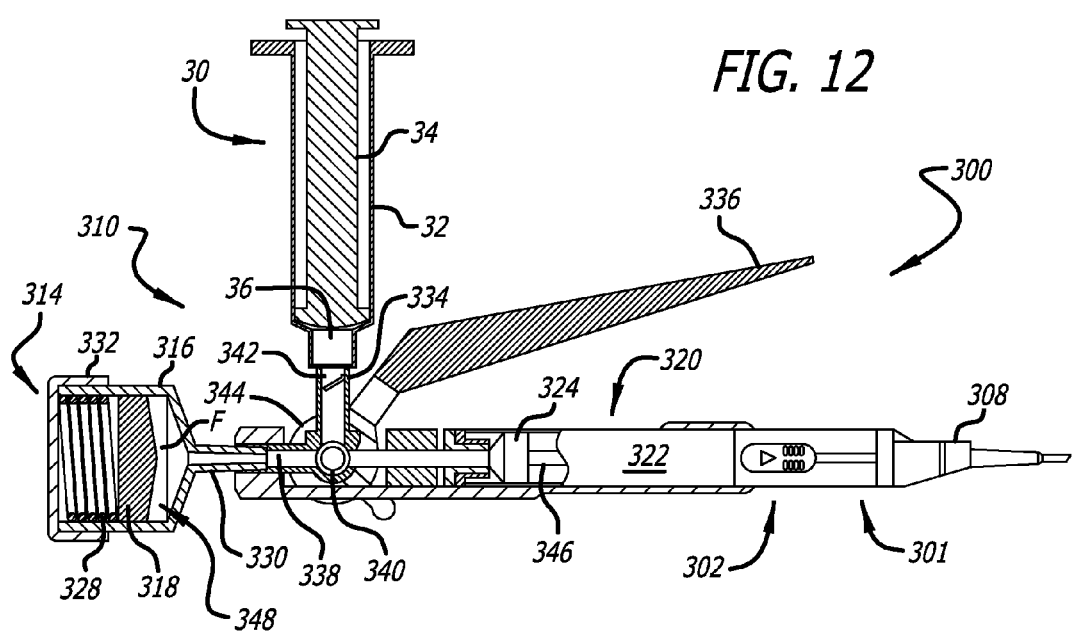
FIG. 12 is a partial section view of the IOL insertion apparatus illustrated in FIG. 9.

One example of a process for priming the plunger driver 310 is illustrated in FIGS. 11-13. This process will in most instances take place while the inserter 301 is located within the case 20 (FIG. 9). In the illustrated example, a syringe 30 is used to prime the plunger driver 310. The syringe includes a barrel 32, a plunger 34 and a hub 36, and is shown filled with hydraulic fluid F. After the handle 336 has been moved to the position illustrated in FIG. 11 (or "priming position"), which causes the valve 340 to direct fluid flow from the fluid port 334 to the master cylinder 314 and prevent fluid flow to the slave cylinder 320, the syringe hub 36 may be connected to the port 334. Next, as shown in FIG. 12, the syringe plunger 32 may be depressed, thereby driving fluid F past the one-way valve 342 and into the master cylinder 314 by way of the valve 340. The fluid F will push the piston 318 to its primed position and compress the spring 328. Movement of the piston 318 also creates a fluid storage volume 348 in which the fluid F is stored when the apparatus 300 is primed.

Turning to FIG. 13, the handle 336 may then be moved to the position illustrated therein (or "primed position"), which causes the valve 340 to prevent flow out of the master cylinder 314. The syringe 30 may then be removed. The case 20 and plunger driver 310 may be configured so as to allow the handle 336 to move from the priming position (FIGS. 11 and 12) to the primed position (FIG. 13) while the insertion apparatus is in the case, but to also prevent the handle from moving to the drive position (FIG. 14) while the insertion apparatus is in the case. To that end, the hub 344 includes a protrusion 350 that is free to move as the handle moves from the priming position to the primed position, and then engages an abutment (not shown) within the case 20 when the handle reaches the primed position.

The primed insertion apparatus 300 may then be removed from the case 20 so as to permit forward movement of the slider 304, which moves the IOL to the transition section of the insertion tube 308 as discussed above with reference to FIGS. 3 and 6, as well as additional movement of the protrusion 350. The plunger driver 310 may then be actuated, and the plunger 306 driven to its extended position, by moving the handle 336 to the drive position illustrated in FIG. 14. The corresponding rotation of the hub 344 will cause the valve 340 to open the fluid path that extends through the tube 338 from the master cylinder 314 to the slave cylinder 320, and to prevent backflow into the port 334. The compressed spring 328 will drive the piston 318 toward the tube 330, thereby driving the fluid F into the slave cylinder 320 so that the piston 324 moves distally through the cylinder body 322 and the plunger moves through the insertion tube 308 to the illustrated location.

Figure 15:
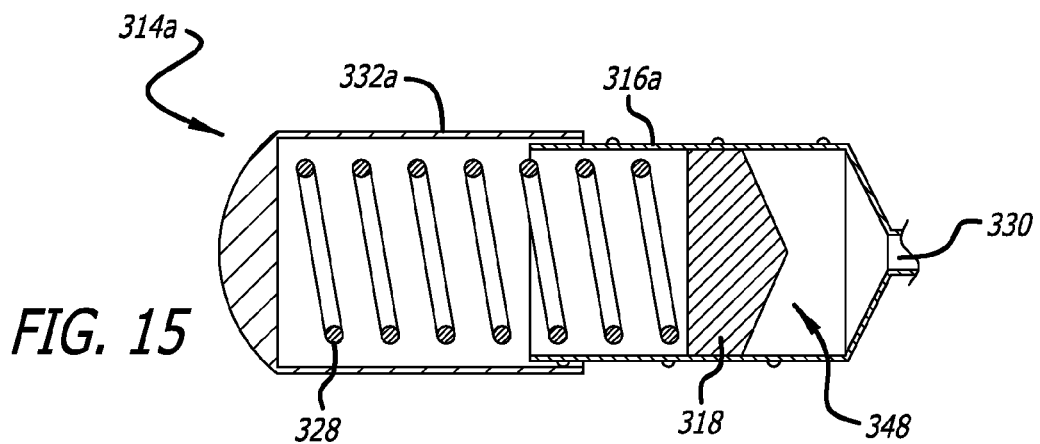
FIG. 15 is a section view of a master cylinder in accordance with one embodiment of a present invention.
Figure 16:
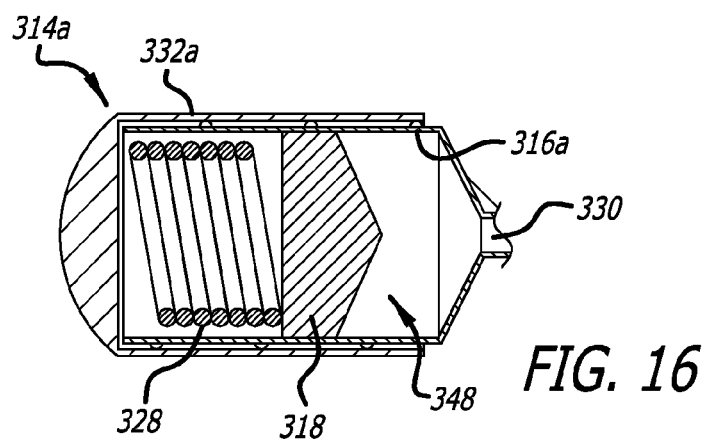
FIG. 16 is a section of the master cylinder illustrated in FIG. 15.
Figure 17:
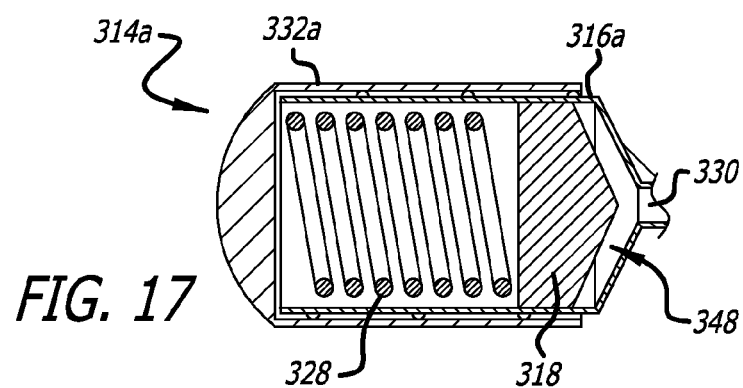
FIG. 17 is a section of the master cylinder illustrated in FIG. 15.

Another apparatus for priming a spring-based master cylinder arrangement is illustrated in FIGS. 15-17. The master cylinder 314*a* includes a cylinder body 316*a*, a piston 318, a spring 328 and a cap 332*a*. The cylinder body 316*a* and cap 332*a* include inner and outer threads, respectively, so that rotation of the cap results in longitudinal movement of the cap relative to the cylinder body. The pre-use state is illustrated in FIG. 15. Fluid may be supplied to the storage volume 348 prior to shipping, or by way of port in the manner described above. With the valve (e.g., valve 340) set to prevent fluid from the master cylinder 314*a*, the cap 332*a* may be rotated to the position illustrated in FIG. 16. The longitudinal movement of cap 332*a* compresses the spring 328 against the piston 318, whose movement is prevented by the fluid, thereby pressurizing the fluid and priming the actuator. The valve may then be opened so that the energy stored in spring 328 can be used to drive the piston 318, as is illustrated in FIG. 17.

Figure 18:
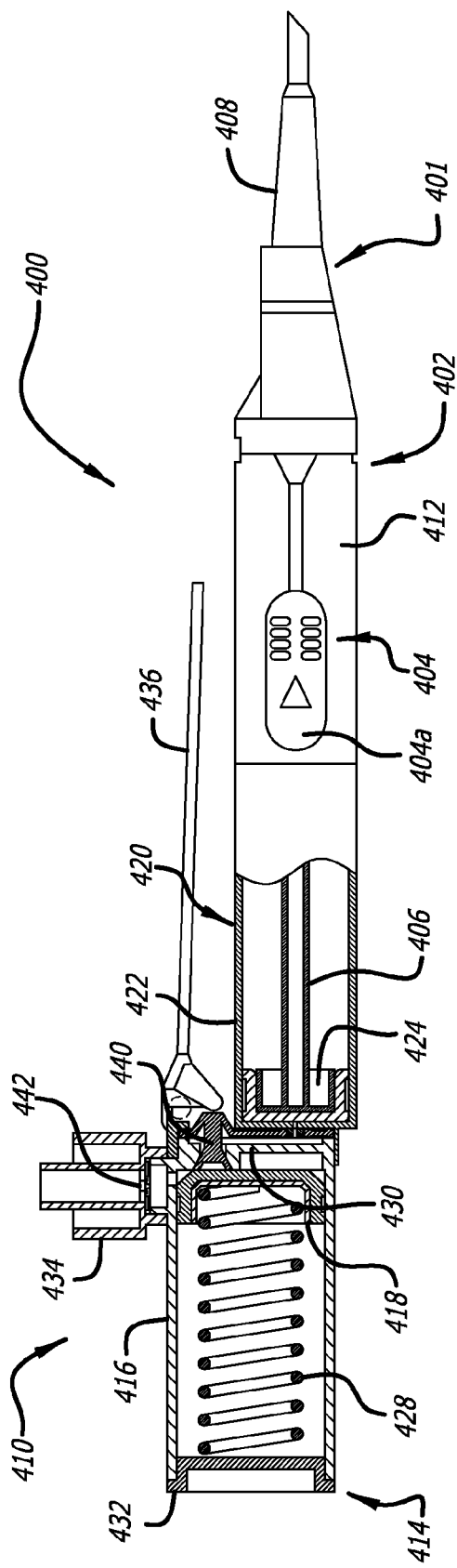
FIG. 18 is a side, partial section view of an IOL insertion apparatus in accordance with one embodiment of a present invention.
Figure 19:
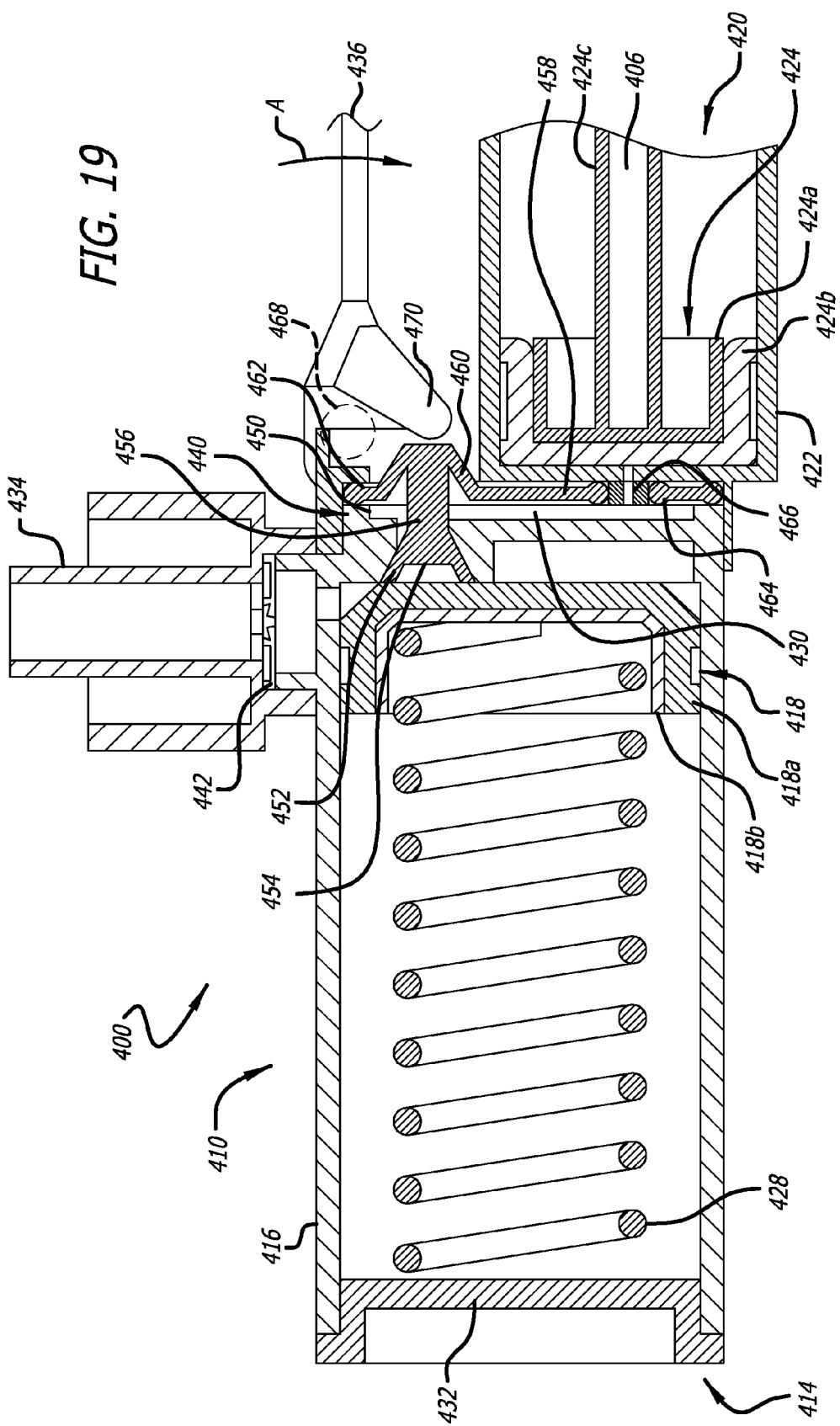
FIG. 19 is a section view of a portion of the IOL insertion apparatus illustrated in FIG. 18.

Another exemplary IOL insertion apparatus is generally represented by reference numeral 400 in FIGS. 18 and 19. Insertion apparatus 400, which includes an inserter 401 and a plunger driver 410, is substantially similar to insertion apparatus 300 and similar elements are represented by similar reference numerals. Like inserter 101, the inserter 401 includes components such as a main body 402 with a tubular member 412, a slider 404 with grips 404*a*, a plunger 406 and an insertion tube 408 which operate in the manner described above with reference to inserter 101. Here too, the plunger driver employs a drive mechanism that is a hybrid device which includes a hydraulic drive mechanism that is powered by a spring. A case, such as case 20 in FIG. 9, may be employed.

The exemplary plunger driver 410 includes a master cylinder 414, with a cylinder body 416 and a piston 418 within the cylinder body, and a slave cylinder 420 with a cylinder body 422 and a piston 424 located within the cylinder body. The inserter 401 is also mounted to a slave cylinder 420 by way of the tubular member 412. An external housing (not shown), similar to the housing 326 in FIG. 10, may be employed in some instances. The piston 418 is driven by a spring 428 that is also located within the cylinder body 416. A fluid path 430 connects the master cylinder 414 to the slave cylinder 420. A cap 432 is used to close the end of the cylinder body 416, after the piston 418 and spring 428 have been inserted, during the assembly process. The plunger driver 410 also includes a fluid port 434 (e.g., the illustrated Luer connector) with a one way valve 442 that receives the hydraulic fluid (e.g., saline) during the priming process, as is discussed below, and an actuation handle 436. Fluid flows directly into the master cylinder 414 through the port 434. A valve 440, which controls flow from the master cylinder 414 to the slave cylinder 420 by way of the fluid path 430, is operably connected to the handle 436.

Referring more specifically to FIG. 19, each of the pistons 418 and 424 in the exemplary plunger driver 410 includes a rigid base and a resilient seal. The piston 418 includes a cup-shaped resilient member 418*a* that prevents fluid leakage and a rigid cup-shaped support member 418*b* that carries the resilient member and anchors the spring 428. The piston 424 includes a cup-shaped resilient member 424*a* that prevents fluid leakage, a rigid cup-shaped support member 424*b* that carries the resilient member, and a longitudinally extending plunger guide 424*c*.

The valve 440 in the illustrated implementation is a self-sealing valve that includes a fluid lumen 450, a valve seat 452 and a valve element 454 that moves in and out of contact with the valve seat to close and open the valve. The valve element 454 is carried on a post 456 that is itself carried by a diaphragm 458. The diaphragm 458 has a conical portion 460, which carries the post 456 and biases the valve element 454 to the closed position, an outer o-ring seal 462, and an inner o-ring seal 464 that surrounds a flow restrictor 466. The handle 436 may be used to open the valve 440. To that end, the handle 436 pivots about a pin 468 and includes a lever 470. Movement of the handle in the direction of arrow A opens the valve 440, and the amount of movement controls the magnitude of the flow and the velocity of the plunger 406.

Figure 20:
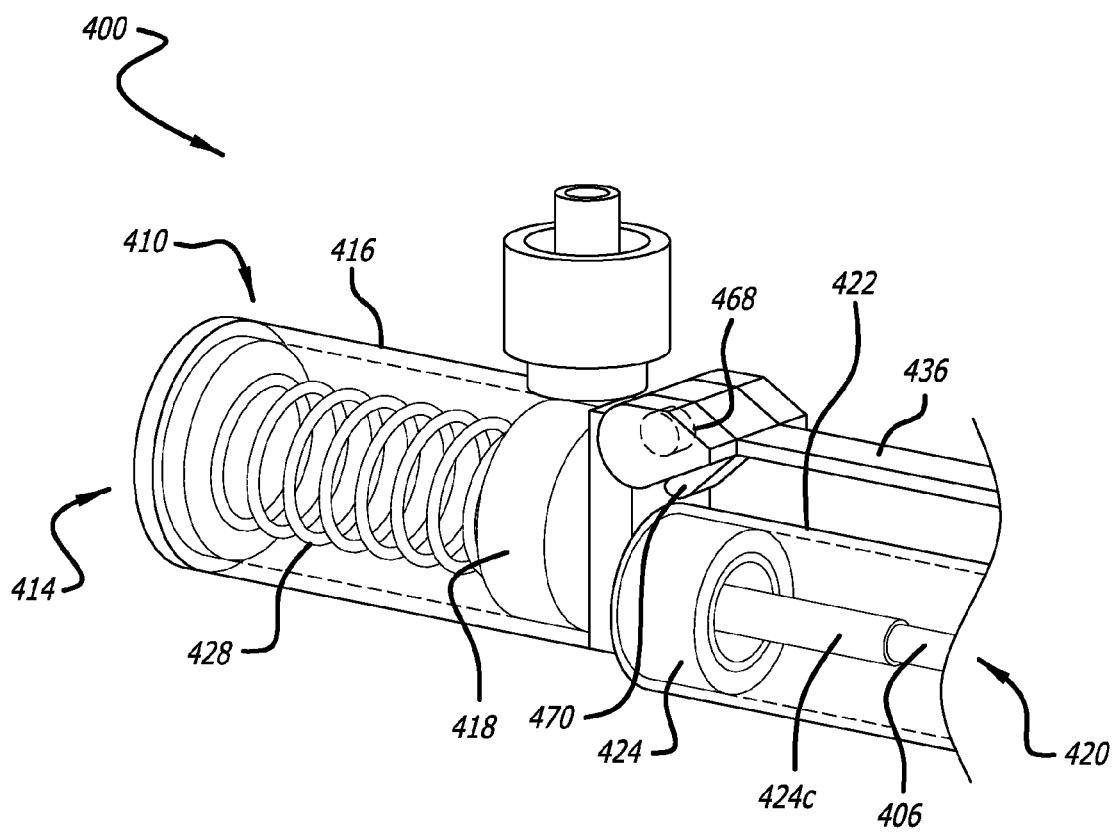
FIG. 20 is a perspective view of a portion of the IOL insertion apparatus illustrated in FIG. 18.
Figure 21:
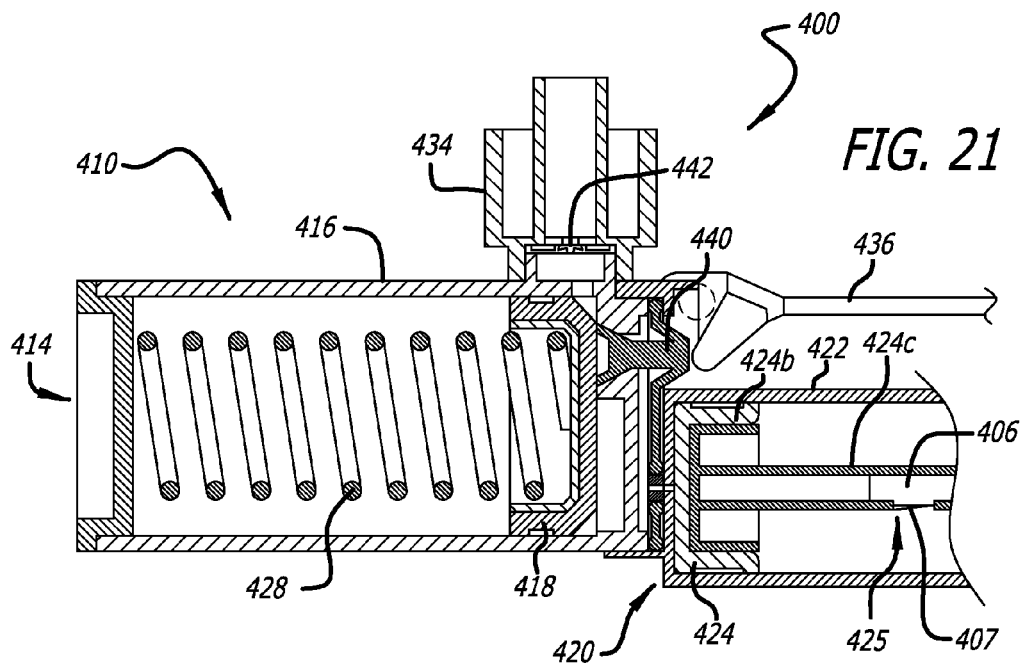
FIG. 21 is a section view of a portion of the IOL insertion apparatus illustrated in FIG. 18.
Figure 22:
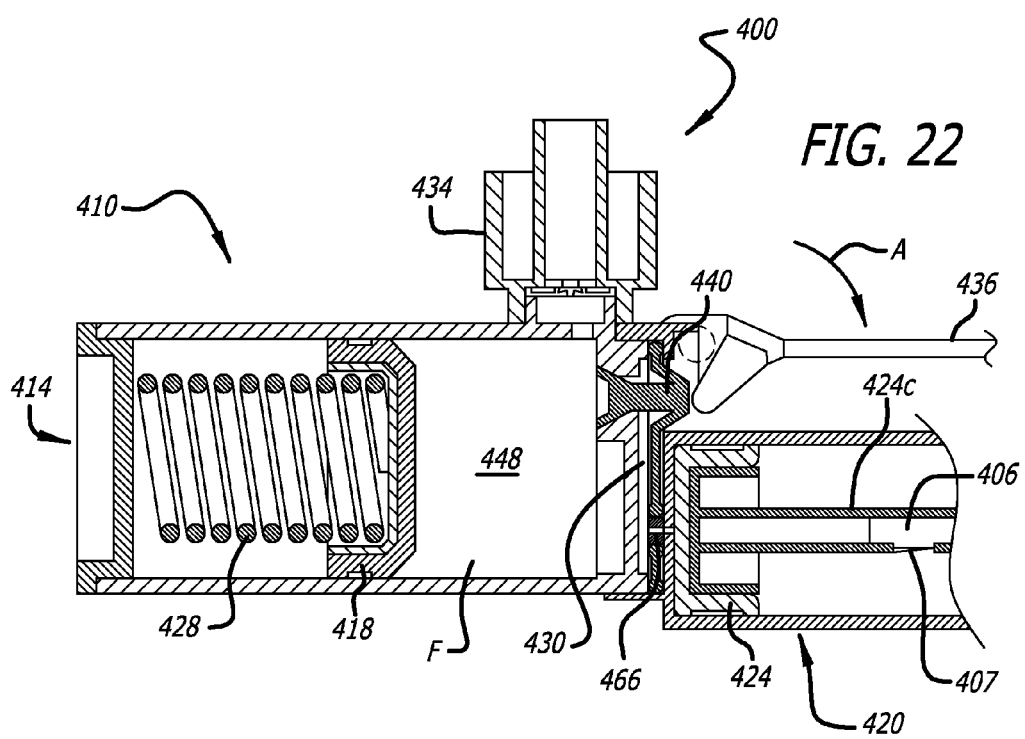
FIG. 22 is a section view of a portion of the IOL insertion apparatus illustrated in FIG. 18.

As illustrated for example in FIGS. 20 and 21, the plunger guide 424*c* includes an aperture 425 near the end of the support member 424*b*, and the plunger 406, which is otherwise similar to plunger 106, includes a depressible projection 407 that is biased to the outwardly deployed state. The plunger 406 and slider 404 are operably connected such that movement of the slider 404 from the pre-use position illustrated FIG. 18 to the use position (note slider 304 in FIG. 14) results in movement of the plunger 406 relative to the plunger guide 424*c* from the position illustrated in FIGS. 19 and 20 to the position illustrated in FIG. 21. When the projection 407 reaches the aperture 425, it will pop into the aperture to connect the plunger 406 to the plunger guide 424*c*. Thereafter, forward movement of the piston 424 will result in forward movement of the plunger 406.

The exemplary plunger driver 410 may be primed with a syringe in a manner similar to the plunger driver 310 when the plunger driver is in the state illustrated in FIG. 21. The force associated with the fluid F being driven into the cylinder body 416 drives the piston 418 back and compresses the spring 428, thereby creating a fluid storage volume 448 (FIG. 22) in which the fluid F is stored under pressure. The force associated with the fluid F being driven into the cylinder body 416 also helps to maintain the valve 440 in its closed state. Thereafter, movement of the handle 436 in the direction of arrow A will open the valve 440, so that fluid can be driven from the master cylinder 414, through the path 430 and flow restrictor 466, and into the slave cylinder 420 to drive the piston 424 and plunger 106*a*. It should be noted that the speed of the plunger 406 may be varied by varying the magnitude of handle 436 movement. The amount of fluid stored in the fluid storage volume 448 is sufficient to drive to the plunger 406 to its fully deployed position and, should the user desire to cease plunger movement prior to the fully deployed position, releasing the handle 436 will allow the valve 440 to return to the closed state to which it is biased.

Figure 23:
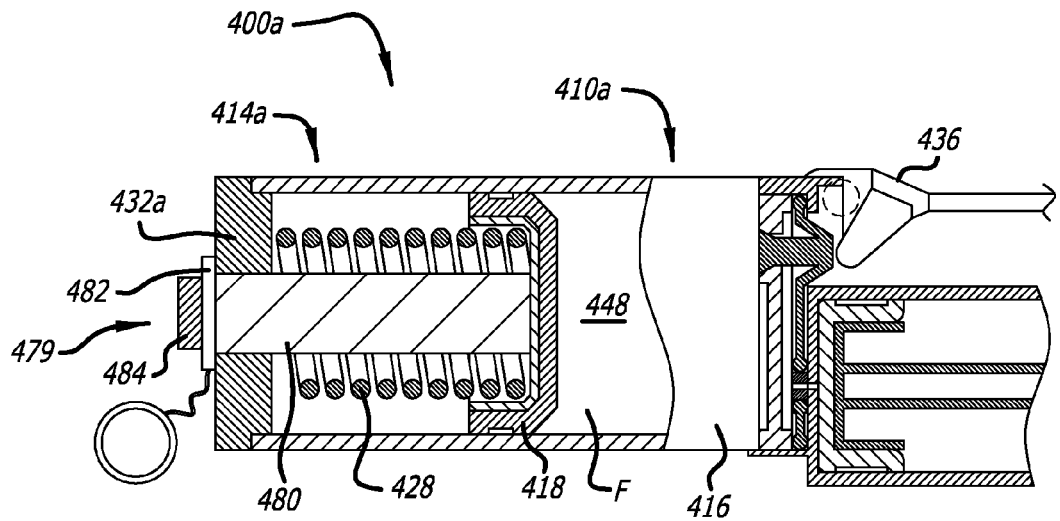
FIG. 23 is a partial section view of a portion of an IOL insertion apparatus in accordance with one embodiment of a present invention.

Hybrid plunger drivers that include a hydraulic drive mechanism powered by a spring, such as those illustrated in FIGS. 9-22, 24A and 24B may be supplied in a primed state with the fluid in the master cylinder and the spring compressed. Structures may be provided to prevent inadvertent actuation of such a driver. Referring to FIG. 23, the exemplary IOL insertion apparatus 400*a* is essentially identical to apparatus 400. Here, however, the storage volume 448 in the plunger driver 410*a* is prefilled with the fluid F during assembly and the spring 428 is pre-compressed. The fluid port 434 may be omitted (as shown), or capped during assembly, depending upon the manner in which fluid is provided to the volume 448. To prevent movement of the piston 418 prior to use, the exemplary master cylinder 414*a* includes a lock 479 which consists of a post 480 that is secured (e.g., welded) to the piston, a cap 432*a* with a aperture for the post, and a pin 482 that extends through a hole 484 in the post. The pin 482 abuts the surface of the cap 432*a*, thereby preventing movement of the post 480 and piston 418, and is held by friction. The pin 482 may be pulled at the time of use so that the piston 418 will move, and fluid will flow, upon rotation of the handle 436.

Figure 24:
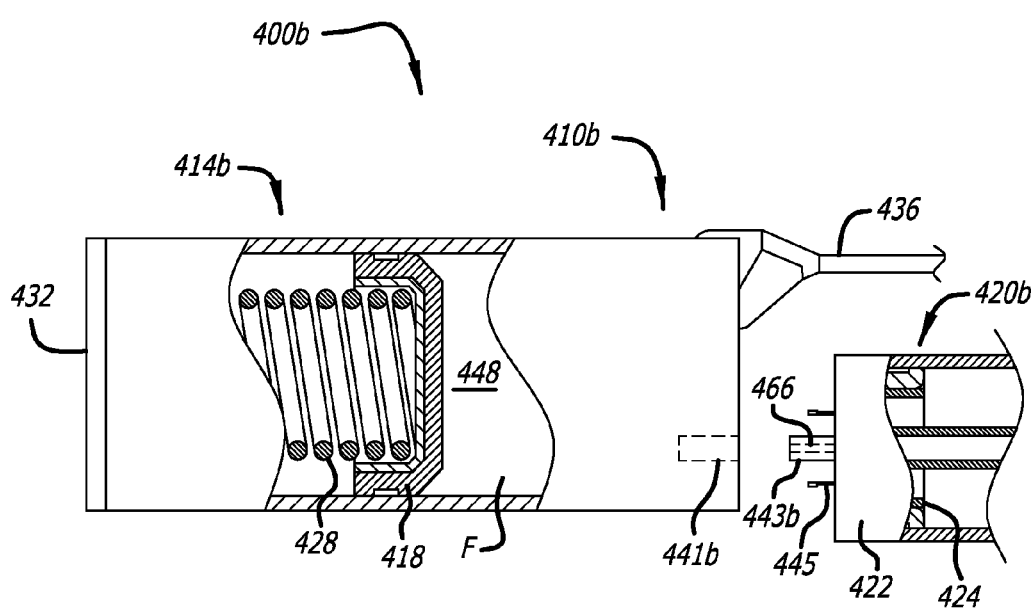
FIG. 24 is a partial section view of a portion of an IOL insertion apparatus in accordance with one embodiment of a present invention.

Turning to FIG. 24, the exemplary IOL insertion apparatus 400*b* is essentially identical to apparatus 400. Here, however, the apparatus is a separable two-piece structure that may be assembled at the time of use. The master cylinder 414*b* of the plunger driver 410*b* is prefilled with fluid F during assembly and the spring 428 is pre-compressed. A normally closed valve 441*b* is aligned with the O-ring seal 464 (note FIG. 19). The slave cylinder 420*b* includes a projection 443*b*, through which the flow restrictor 466 extends, which is configured to open the valve 441*b* when the master and slave cylinders are attached to one another at the time of use. To that end, the slave cylinder 420*b* includes one or more connectors (e.g., connectors 445) that mate with corresponding connectors (e.g., apertures) on the master cylinder 414*b*. The spring-based insertion apparatus described with below may also be configured as two-piece separable structures.

Figure 24A:
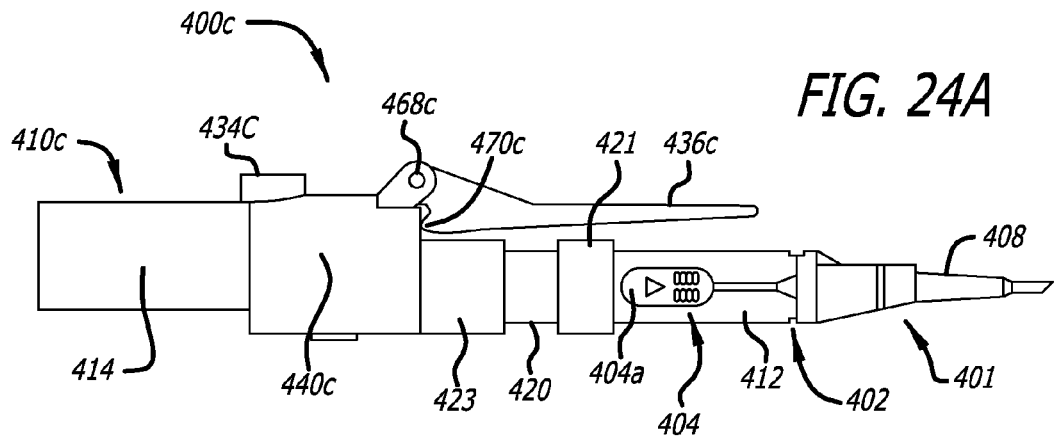
FIG. 24A is a side view of an IOL insertion apparatus in accordance with one embodiment of a present invention.
Figure 24B:
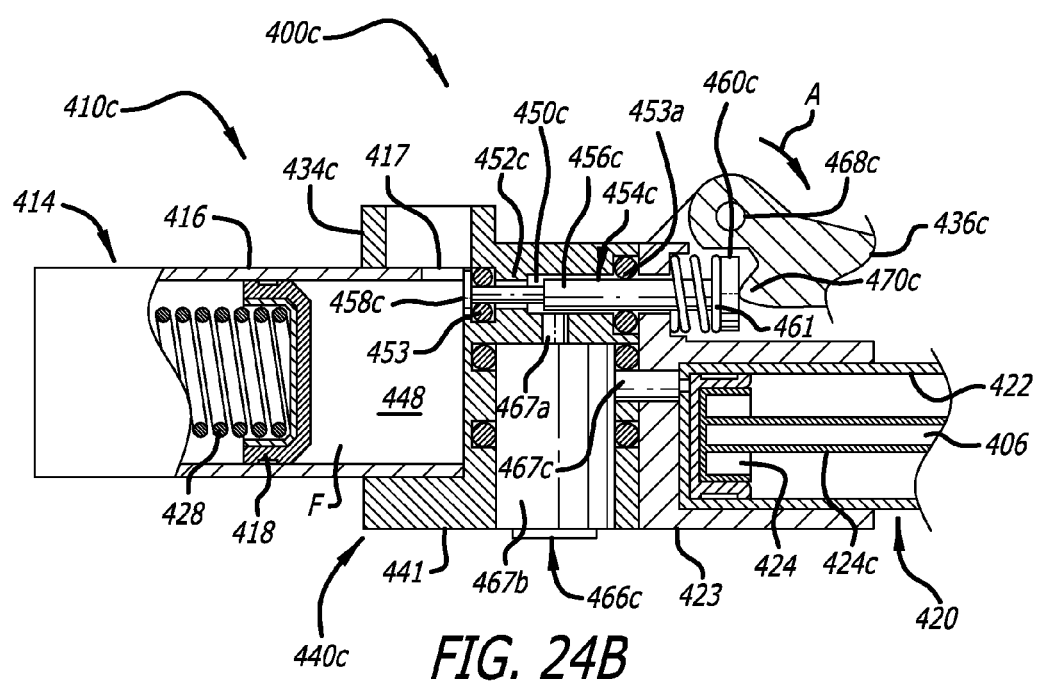
FIG. 24B is a side, partial section view of a portion of the IOL insertion apparatus illustrated in FIG. 24A.

Another exemplary IOL insertion apparatus is generally represented by reference numeral 400*c* in FIGS. 24A and 24B. Insertion apparatus 400*c*, which includes an inserter 401 and a plunger driver 410*c*, is substantially similar to insertion apparatus 400 and similar elements are represented by similar reference numerals. For example, the inserter 401 includes components such as a main body 402 with a tubular member 412, a slider 404 with grips 404*a*, a plunger 406 and an insertion tube 408 which operate in the manner described above with reference to inserter 101. Here too, the plunger driver employs a drive mechanism that is a hybrid device which includes a hydraulic drive mechanism that is powered by a spring. A case, such as case 20 in FIG. 9, may be employed. The plunger 406 and plunger guide 424*c* are configured, and operate in conjunction with the slider 404, in the manner described above.

The exemplary plunger driver 410*c* includes the above-described master cylinder 414, with a cylinder body 416 and a piston 418 within the cylinder body, and a slave cylinder 420 with a cylinder body 422 and a piston 424 located within the cylinder body. The slave cylinder 420 may be a permanent part of the insertion apparatus, or a removable part in the manner discussed above with reference to FIG. 24. The inserter 401 is mounted to the slave cylinder 420 by way of a connector tube 421. An external housing (not shown), similar to the housing 326 in FIG. 10, may be employed in some instances. The piston 418 is driven by a spring 428 that is also located within the cylinder body 416. A valve 440c, including a handle 436c that allows the user to open and close the valve, connects the master cylinder 414 to the slave cylinder 420 and establishes a controllable fluid path therebetween. A bracket 423 mounts the slave cylinder 420 to the valve 440c.

Referring more specifically to FIG. 24B, the valve 440c is a self-sealing valve that includes a housing 441, a fluid lumen 450c, a valve seat 452c and a valve element 454c that moves in and out of contact with an o-ring seal 453 on the valve seat to close and open the valve. The valve element 454c is movable between a closed position, a fully open position, and a plurality of partially open positions therebetween. The other end of the fluid lumen 450c is sealed with an o-ring seal 453a. The valve element 454c includes a post 456c, a valve member 458c and a spring support 460c. A spring 461 biases the valve element to the closed position. A flow restrictor 466c establishes a fluidic connection between the fluid lumen 450c and the slave cylinder 420. In the illustrated implementation, the flow restrictor 466c is a needle valve, including an inlet port 467a, a main portion 467b and an outlet port 467c, that may be preset to the desired amount of restriction. The actuator handle 346c pivots about a pin 468c and includes a lever 470c that presses on the valve element 454c. Movement of the handle 436c in the direction of arrow A overcomes the biasing force of the spring 461 and opens the valve 440c, and the amount of movement controls the magnitude of the flow and the velocity of the plunger 406.

The exemplary plunger driver 410 may be primed with hydraulic fluid from a syringe in the manner described above. To that end, the valve housing 441 includes a connector 434c for a fluid port (e.g., the Luer connector 434 with the one way valve 442 illustrated in FIG. 19). An aperture 417 in the cylinder body 416 allows flow from the connector to the fluid storage volume 448.

It should also be noted that, in other implementations, other types of valves may be employed in place of those described above with reference to FIGS. 9-24B. Other exemplary valves that may be employed include solenoid actuated valves that are connected to a button.

Figure 25:
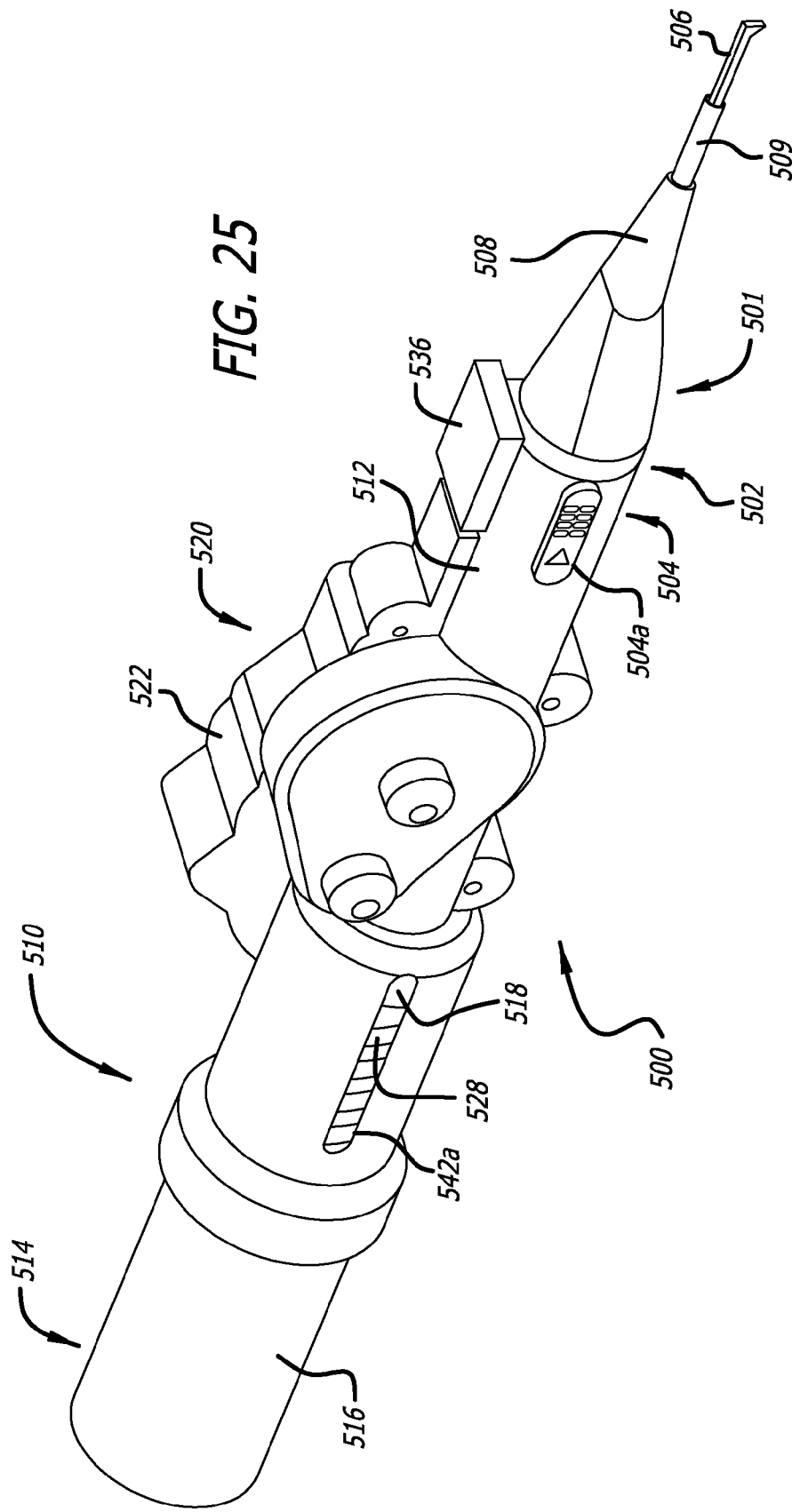
FIG. 25 is perspective view of an IOL insertion apparatus in accordance with one embodiment of a present invention.
Figure 26:
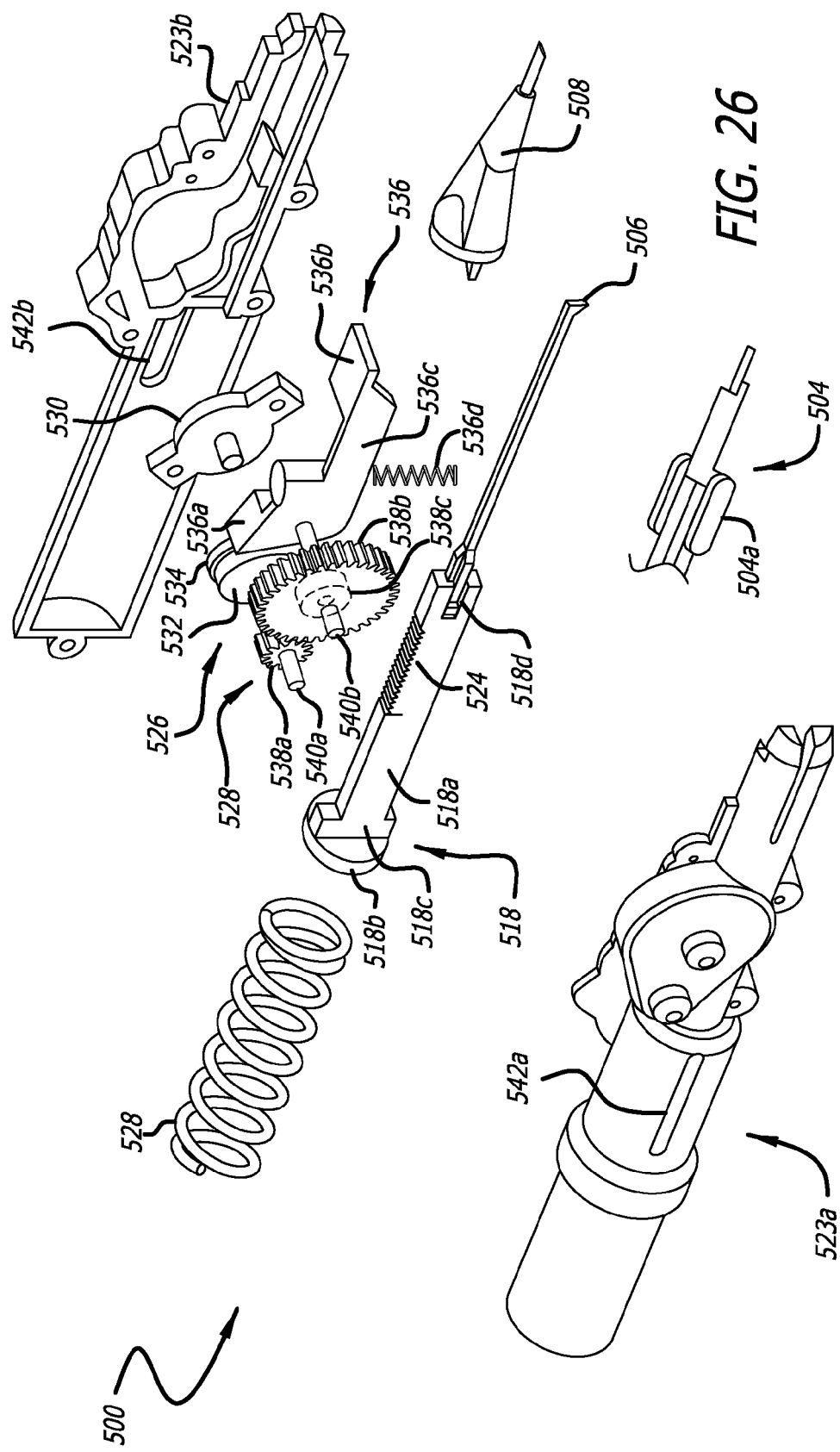
FIG. 26 is an exploded view of the IOL insertion apparatus illustrated in FIG. 25.

Another exemplary IOL insertion apparatus is generally represented by reference numeral 500 in FIGS. 25 and 26. The exemplary insertion apparatus 500 includes an inserter 501 and a plunger driver 510. The inserter 501 is substantially similar to the inserter 101 and similar elements are represented by similar reference numerals. To that end, the inserter 501 includes components, such as a main body 502 with a tubular member 512, a slider 504 with grips 504a, a plunger 506 and an insertion tube 508 that together operate in the manner described above with reference to inserter 101. A case similar to case 20 may be employed to prevent erroneous operation of the insertion apparatus.

The exemplary plunger driver 510 illustrated in FIGS. 25 and 26 is a spring-driven device that includes a drive portion 514 and a control portion 520. The drive portion includes a housing 516, a piston 518 that is connected to the plunger 506 and to the control portion 520 (as discussed below), and a spring 528. The piston 518 has an elongate piston body 518a, abutments 518b and 518c and a connector 518d at the other end for the plunger 506. The circular abutment 518b is in contact with the spring 528 and slides along the inner surface of the housing 516. Abutment 518c connects the abutment 518b to the piston body 518a. In other implementations, the plunger and piston may be formed as a single, integral unit. The control portion 520 includes a housing 522, a rack 524 that is secured to the piston 518, a brake 526, a gear train 528 that connects the brake 526 to the rack 524, and a rotary damper 530 that limits the forward acceleration of the gear train (and components connected thereto) without necessitating an increase in spring force. In the illustrated implantation, the main body 502, housing 516 and housing 522 are commonly formed by a two-part structure consisting of housing part 523a and housing part 523b (FIG. 26).

Figure 27:
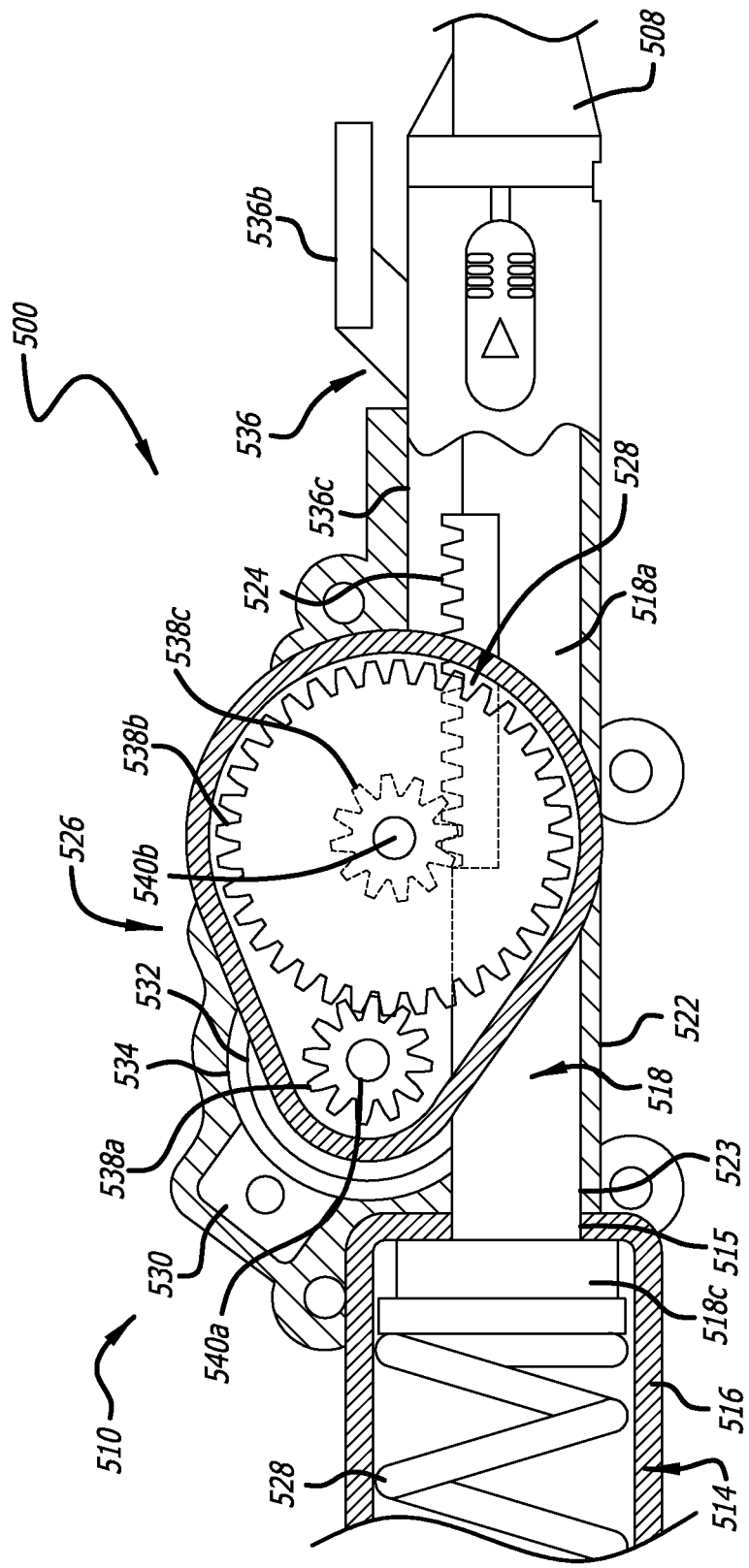
FIG. 27 is a side, partial cutaway view of the IOL insertion apparatus illustrated in FIG. 25.

The piston 518 has portions located within, and moveable relative to, both the drive portion 514 and a control portion 520. Referring to FIG. 27, the drive portion housing 516 includes an aperture 515 and the control portion housing 22 includes a corresponding aperture 523 through which the piston 518 extends. The aperture 515 is smaller than the abutment 518c, which limits the distance that the piston 518 can travel.

Figure 28:
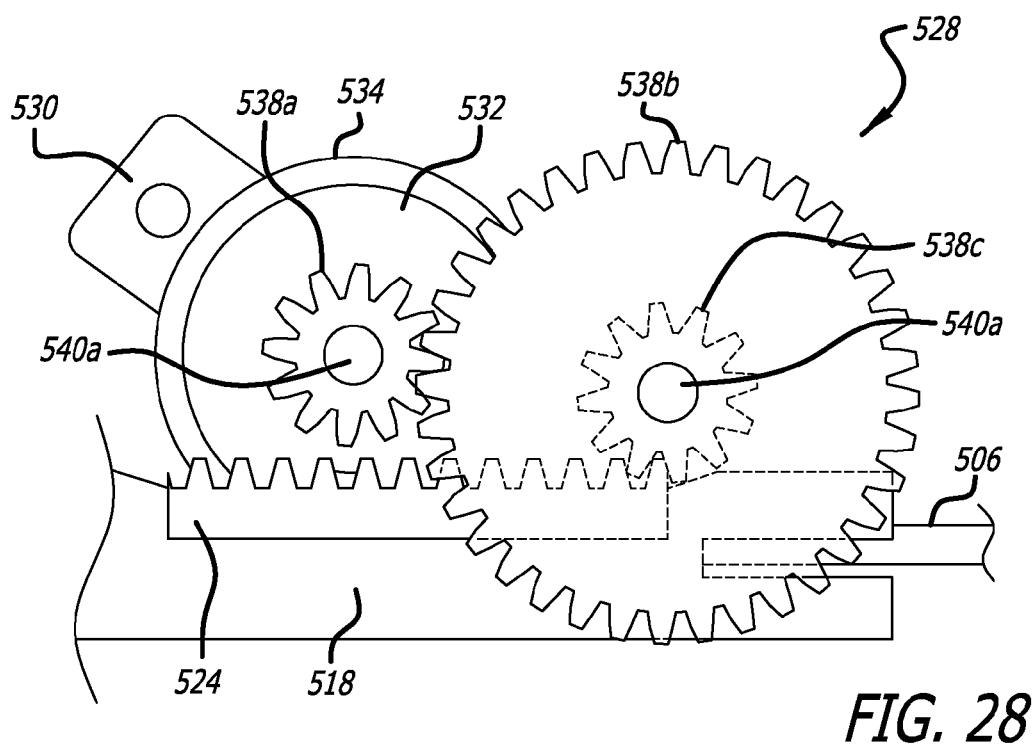
FIG. 28 is a side view of a portion of the IOL insertion apparatus illustrated in FIG. 25.

As illustrated in FIGS. 26-28, the exemplary brake 526 has a drum 532, a friction element 534 (e.g., a rubber O-ring), and an actuator 536. The actuator 536 includes an engagement element 536a that is connected to a button 536b by a lever 536c. The engagement element 536a engages the friction element 534 on the drum 532, while the lever 536c is pivotably mounted on the gear axle 540b (discussed below) and is biased by a spring 536d to an orientation that results in the engagement element 536a engages the friction element 534 with sufficient force to stop spring driven movement of the piston 516 and plunger 506. The exemplary gear train 528, which is a two-stage gear train, includes gears 538a, 538b and 538c. Gear 538a and brake drum 532 are both mounted on axle 540a, which is the axle of the rotary damper 530, and gears 538b and 538c are mounted on axel 540b. Gear 538a meshes with gear 538b. Gear 538c engages the rack 524 such that linear movement of the piston 518 results in rotation of the gear 538c. Conversely, slowing or preventing rotation of the brake drum 532 slows or prevents spring driven linear movement of the piston 518. The gear train 528 allows the torque input to the rotary damper 530 to be minimized, and also minimizes the amount of braking force required to prevent rotation of the gears and forward movement of the rack 524 and piston 518. The two-stage gear train gear train 528 also facilitates a smaller device as compared to a device with a single gear connected to the brake and rack.

The spring 528 is compressed during the assembly process and may be maintained in the compressed state in a variety of ways. For example, the brake 526 may be configured such that the piston 518 will not move unless a significant amount of force (i.e., a force greater than that associated with shipping, handling, etc.) is applied to the button 536b. Alternatively, or in addition, the case may be configured so as to prevent depression of the button 536b during storage. Another alternative is placing a removable wedge-like structure (not shown) between the underside of the button 536b and the adjacent portion of the inserter 501. Still another alternative is a pin (not shown) that may be inserted through a hole in the housing and into the region where gears 538a and 538c mesh to prevent rotation thereof.

Figure 29:
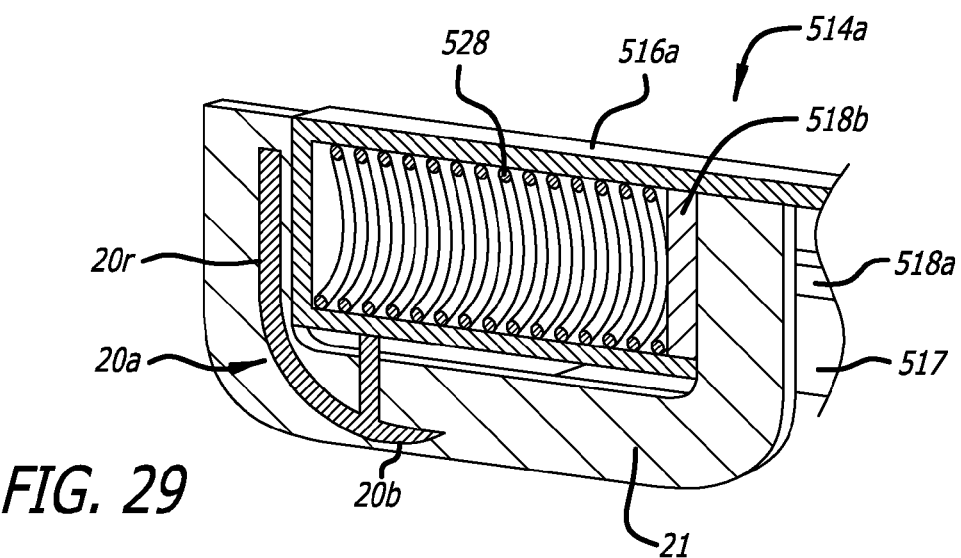
FIG. 29 is a section view showing portions of a plunger driver and a case in accordance with one embodiment of a present invention.

Structures that act directly on the piston and/or spring to prevent expansion of the compressed spring may also be employed during shipping and storage. For example, and referring to FIGS. 25 and 26, the exemplary drive portion housing 516 includes a pair of longitudinally extending apertures 542a and 542b. A wedge-like structure (not shown) that extends the length of the aperture and engages the circular abutment 518b on the piston 518 may be inserted into one or both of the apertures 542a and 542b. Turning to FIG. 29, the exemplary drive portion 514a and case 20a are configured to maintain the spring 528 in the compressed state and prevent movement of the piston. Here, the case 20a includes a rigid member 21 that projects into the storage area, and the drive portion housing 516a include a slot 517 that is located adjacent to the circular abutment 518b, and is offset from the piston body 518a and abutment 518c. In the illustrated implementation, the rigid member 21 is a generally U-shaped metal structure that is molded into the bottom wall 20b and rear wall 20r of the case 20a. In still other implementations, a master cylinder that is pressurized at the time of use (similar to that illustrated in FIGS. 15-17) may be employed.

Figure 30:
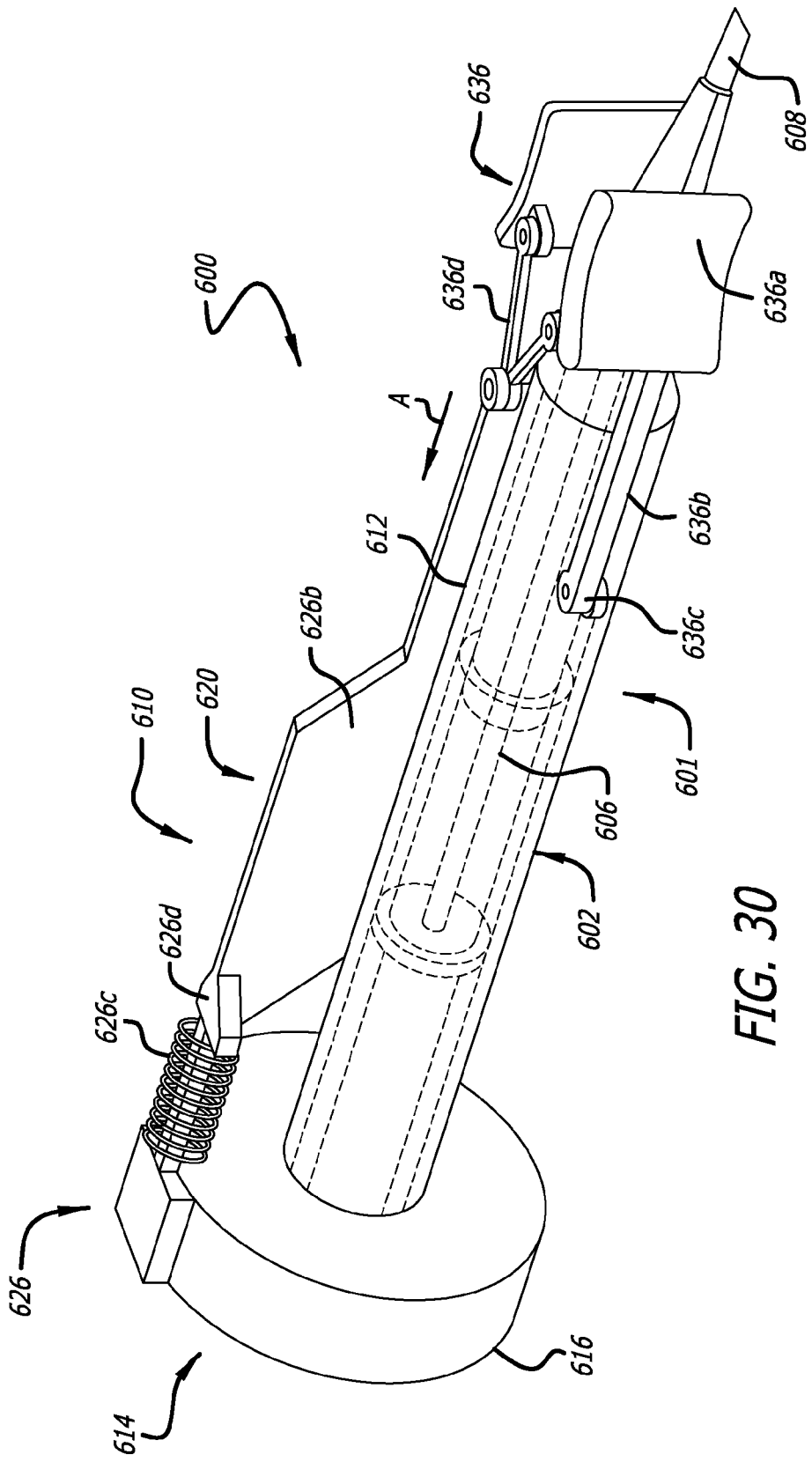
FIG. 30 is perspective view of an IOL insertion apparatus in accordance with one embodiment of a present invention.
Figure 31:
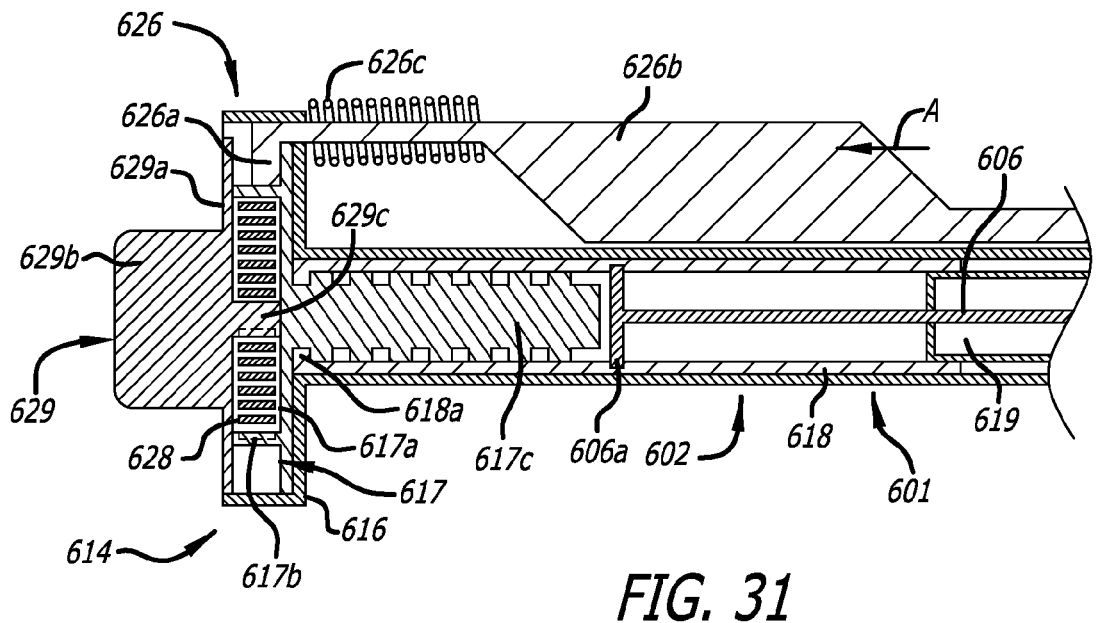
FIG. 31 is a section view of the IOL insertion apparatus illustrated in FIG. 30.
Figure 32:
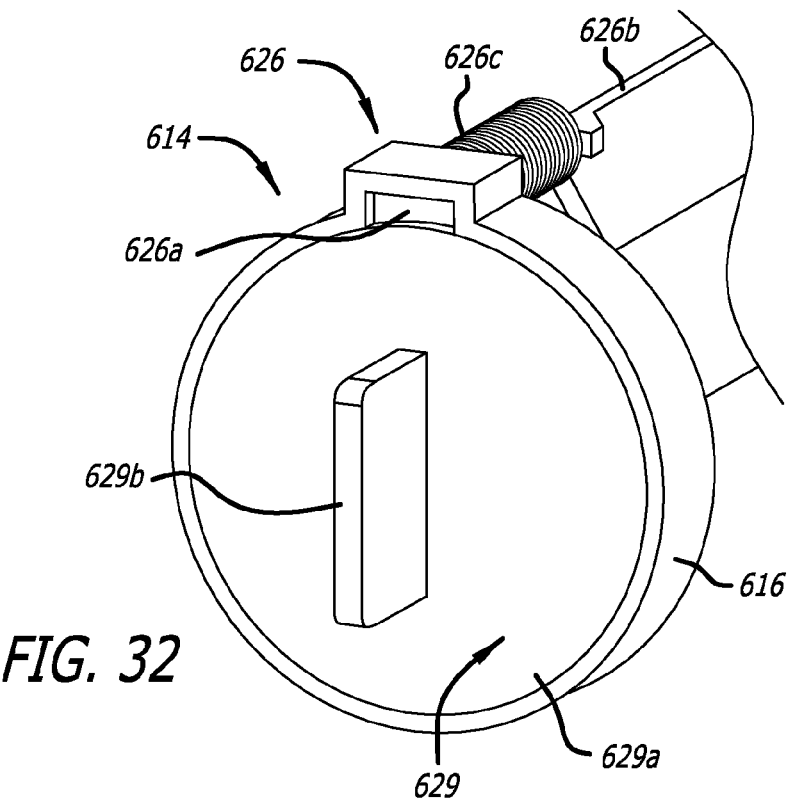
FIG. 32 is a rear perspective view of a portion of the IOL insertion apparatus illustrated in FIG. 30.

Another exemplary IOL insertion apparatus is generally represented by reference numeral 600 in FIGS. 30-32. The exemplary insertion apparatus 600 includes an inserter 601 and a plunger driver 610. The inserter 601 includes a main body 602 with a tubular member 612, a plunger 606, and an insertion tube 608 that together operate in the manner described above with reference to inserter 101. Unlike other inserters described herein, the inserter 601 does not include a slider. The lens is pushed from the storage area and though the insertion tube 608 with the plunger 606. A case similar to case 20 may be employed to prevent erroneous operation of the insertion apparatus, as is discussed below. The exemplary plunger driver 610 is a spring-driven device that includes a drive portion 614 and a control portion 620.

The drive portion 614 in the illustrated embodiment includes a housing 616, a rotatable hub 617 located within the housing, a piston 618 that located within the tubular member 612 and connected to a mounting member 606a on the plunger 606 and to the rotatable hub 617, a spiral torsion spring (or "mainspring") 628, and a winding arbor 629. The rotatable hub 617 includes a disk 617a, a cylindrical member 617b, and an externally threaded member 617c. The winding arbor 629 includes a disk 629a, a handle 629b and an axle 629c. The outer end of the mainspring 628 is secured to the hub cylindrical member 617b and the inner end of the mainspring is secured to the arbor axle 629c. The rotatable hub 617 is connected to the piston 618 by way of an internally threaded member 618a at one end of the piston that engages the threads on the externally threaded member 617c. The piston 618 is also keyed to the outer surface of a guide 619 in such a manner rotational motion of the piston is prevented and longitudinal movement is permitted. Thus, rotational motion of the hub 617 is translated into linear movement of the piston 618 and plunger 606.

The exemplary control portion 620 prevents, and selectively allows upon user action, rotation of the hub 617. To that end, the control portion includes a brake 626 and a brake control apparatus 636. The brake 626 has an engagement element 626a, that is connected to the brake control apparatus 636 by an elongate member 626b, and a spring 626c that biases the brake to the rotation prevention position illustrated in FIG. 31. The spring 626c, which is compressed between the drive portion housing 616 and an abutment 626d on the elongate member 626b, exerts sufficient force on the engagement element 626a (by way of the elongate member) to prevent rotation of the hub 617. The control apparatus 636 includes a pair of finger tabs 636a that are pivotably mounted on the tubular member 612 with arms 636b and pivot pins 636c. The finger tabs 636a are also secured to a flexible V-shaped member 636d that is itself connected to the brake elongate member 626b. Movement of the finger tabs 636a toward one another increases the length of the V-shaped member 636d which, in turn, drives the brake elongate member 626b in the direction of arrow A and separates the engagement element 626a from the hub disk 617a. The hub 617 will then be rotated by the mainspring 628.

During assembly, and with the brake 626 preventing rotation of the hub 617, the winding arbor 629 is rotated to wind the mainspring 628. Rotation of the axle 629c rotates the associated end of the mainspring 628 while rotation of the other end is prevented by virtue of its connection to the hub 617. When the winding is complete, the winding arbor disk 629a may be fixedly secured to the housing 616, thereby prevent rotation of the winding arbor 629, by mechanical fasteners, adhesive, welding or other suitable instrumentalities.

The insertion apparatus 600 may be shipped and stored in a manner that prevents unwinding of the mainspring 628 prior to use. For example, the housing 616 and hub disk 617a may be provided with apertures that will be aligned with one another after the mainspring 628 is wound, and pins may be inserted through the apertures to prevent rotation of the hub 617 relative to the housing. A blocking structure that prevents the finger tabs 363a from moving toward one another may be provided as part of a case that is similar to case 20, or as a separate device. A case that prevents longitudinal movement of the piston 618 in a manner to that similar to the case described above with reference to FIG. 29 may also be provided.

Numerous other modifications and/or additions to the above-described preferred embodiments would be readily apparent to one skilled in the art. For example, insertion apparatus in accordance with the present inventions may consist of a re-usable, non-manually powered inserter that is combined with an IOL cartridge (either a preloaded cartridge or a cartridge that is loaded at the time of the surgical procedure) to form the insertion apparatus. Such a cartridge may include a IOL storage region where the IOL is stored in a flat, unstressed state, a nozzle, and a tapered region therebetween. The present inventions are also applicable to inserters without sliders, as is alluded to above, and any of the insertion apparatus described herein may be reconfigured so as to exclude sliders. Alternatively, the plunger drivers and sliders described above may be reconfigured such that the plunger drivers drive the slider in addition to the plunger at the time of use. It is intended that the scope of the present inventions extends to all such modifications and/or additions.

We claim:

1. An ocular implant insertion apparatus, comprising:
   a housing including an ocular implant storage area and a nozzle;
   a plunger movable in a distal direction relative to the housing;
   a hybrid spring-based and hydraulic plunger driver, including a master cylinder and a slave cylinder, that is configured to drive the plunger in the distal direction, the master cylinder including a cylinder body, a piston, a spring and a threaded cap that moves longitudinally on the cylinder body and compresses the spring in response to rotation of the threaded cap relative to the cylinder body;
   a fluid port; and
   a multi-position valve operably connected to the master cylinder, the slave cylinder and the fluid port, and having a first position where the multi-position valve connects the master cylinder to the fluid port and disconnects the master cylinder from the slave cylinder, a second position where the multi-position valve disconnects the master cylinder from the fluid port and from the slave cylinder, and a third position where the multi-position valve disconnects the master cylinder from the fluid port and connects the master cylinder to the slave cylinder.

2. The ocular implant insertion apparatus as claimed in claim 1, wherein the multi-position valve comprises a variable flow valve that is movable between a plurality of partially open positions where the master cylinder is disconnected from the fluid port and is connected to the slave cylinder.

3. The ocular implant insertion apparatus as claimed in claim 2, further comprising:
a handle associated with the variable flow valve such that movement of the handle results in movement of the variable flow valve.

4. The ocular implant insertion apparatus as claimed in claim 1, further comprising:
an ocular implant stored within the housing in a substantially unstressed state.

5. The ocular implant insertion apparatus as claimed in claim 1, further comprising:
a slider configured to fold an ocular implant as the slider moves from a first slider position to a second slider position.

6. The ocular implant insertion apparatus as claimed in claim 5, wherein the slider includes a pivotable structure that folds the ocular implant as the slider moves.

7. The ocular implant insertion apparatus as claimed in claim 5, wherein the plunger is movable relative to the slider.

8. The ocular implant insertion apparatus as claimed in claim 7, wherein the housing is configured such that the ocular implant is further folded when being moved by the plunger.

9. The ocular implant insertion apparatus as claimed in claim 1, wherein the ocular implant storage area comprises an IOL storage area.

10. The ocular implant insertion apparatus as claimed in claim 1, further comprising:
an IOL heater.

11. The ocular implant insertion apparatus as claimed in claim 1, further comprising:
a control instrumentality configured to control operation of the hybrid spring-based and hydraulic plunger driver.

12. An ocular implant insertion apparatus, comprising:
a housing including an ocular implant storage area and a nozzle;
a plunger movable in a distal direction relative to the housing;
a hybrid spring-based and hydraulic plunger driver, including a master cylinder with a fluid storage volume, a spring and a piston, and a slave cylinder with a piston that is connected to the plunger, that is configured to drive the plunger in the distal direction as the spring moves from a compressed state to a less compressed state;
a fluid port, including a one-way valve that opens in response to fluid being driven into the port, in fluid communication with the master cylinder fluid storage volume; and
a multi-position valve, operably connected to the master cylinder and the slave cylinder, having a first position where the multi-position valve connects the master cylinder to the slave cylinder and a second position where the multi-position valve disconnects the master cylinder from the slave cylinder.

13. The ocular implant insertion apparatus as claimed in claim 12, further comprising:
a handle associated with the multi-position valve such that movement of the handle results in movement of the multi-position valve.

14. The ocular implant insertion apparatus as claimed in claim 12, further comprising:
an ocular implant stored within the housing in a substantially unstressed state.

15. The ocular implant insertion apparatus as claimed in claim 12, further comprising:
a slider configured to fold an ocular implant as the slider moves from a first slider position to a second slider position.

16. The ocular implant insertion apparatus as claimed in claim 12, wherein the ocular implant storage area comprises an IOL storage area.

17. The ocular implant insertion apparatus as claimed in claim 12, further comprising:
a control instrumentality configured to control operation of the hybrid spring-based and hydraulic plunger driver.

18. An ocular implant insertion method, comprising the steps of:
driving fluid with a syringe into a hybrid spring-based and hydraulic plunger driver, which includes a master cylinder with a spring and a piston and a slave cylinder with a piston that is connected to a plunger, to compress the spring while fluid flow from the master cylinder to the slave cylinder and associated movement of the plunger is prevented; and
pushing an ocular implant out of an ocular implant storage area and through a nozzle of an insertion apparatus with the hybrid spring-based and hydraulic plunger driver by permitting fluid flow from the master cylinder to the slave cylinder and driving fluid out of the master cylinder by pushing the piston with the spring.

* * * * *